(12) United States Patent
Murata et al.

(10) Patent No.: US 7,825,275 B2
(45) Date of Patent: Nov. 2, 2010

(54) FLUORINATED COMPOUND, FLUOROPOLYMER AND METHOD FOR PRODUCING THE COMPOUND

(75) Inventors: Koichi Murata, Chiyoda-ku (JP); Naoko Shirota, Chiyoda-ku (JP); Osamu Yokokoji, Chiyoda-ku (JP); Yoko Takebe, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/567,932

(22) Filed: Sep. 28, 2009

(65) Prior Publication Data

US 2010/0016532 A1 Jan. 21, 2010

Related U.S. Application Data

(63) Continuation of application No. PCT/JP08/52896, filed on Feb. 20, 2008.

(30) Foreign Application Priority Data

Mar. 30, 2007 (JP) .............................. 2007-093221
Oct. 4, 2007 (JP) .............................. 2007-261185

(51) Int. Cl.
 *C07C 51/09* (2006.01)
 *C07C 51/38* (2006.01)
 *C07C 57/52* (2006.01)
 *C07C 67/04* (2006.01)
 *C07C 67/343* (2006.01)
 *C07C 69/65* (2006.01)

(52) U.S. Cl. ..................... 560/219; 560/190; 562/598

(58) Field of Classification Search ................. None
 See application file for complete search history.

(56) References Cited

U.S. PATENT DOCUMENTS

| 4,910,276 | A | 3/1990 | Nakamura et al. |
| 6,818,258 | B2 | 11/2004 | Kaneko et al. |
| 6,858,692 | B2 | 2/2005 | Kaneko et al. |
| 7,091,294 | B2 | 8/2006 | Takebe et al. |
| 7,244,545 | B2 | 7/2007 | Takebe et al. |
| 7,550,545 | B2 | 6/2009 | Takebe et al. |
| 2006/0122348 | A1 | 6/2006 | Takebe et al. |
| 2009/0221845 | A1 | 9/2009 | Takebe et al. |

FOREIGN PATENT DOCUMENTS

| JP | 9-502429 | 3/1997 |
| JP | 2000-511192 | 8/2000 |
| JP | 2005-60664 | 3/2005 |
| JP | 2005-298707 | 10/2005 |
| JP | 2007-131683 | 5/2007 |
| WO | 2005-023734 | 3/2005 |

OTHER PUBLICATIONS

Sasaki, T. et al., Journal of Photopolymer Science and Technology, 2004, 17(4), pp. 639-644.

*Primary Examiner*—Daniel M Sullivan
*Assistant Examiner*—Yevegeny Valenrod
(74) *Attorney, Agent, or Firm*—Oblon, Spivak, McClelland, Maier & Neustadt, L.L.P.

(57) ABSTRACT

To provide a novel fluorinated compound, a fluoropolymer and a method for producing the compound.

A compound represented by the formula $CF_2=CFCF_2C(X)(C(O)OZ)(CH_2)_nCR=CHR$ (wherein X is a hydrogen atom, a cyano group or a group represented by the formula $—C(O)OZ$, Z is a hydrogen atom or a $C_{1-20}$ monovalent organic group, n is 0, 1, or 2, and R is a hydrogen atom or a $C_{1-20}$ monovalent organic group), a method for producing it, and a fluoropolymer obtained by polymerizing the compound.

11 Claims, No Drawings

FLUORINATED COMPOUND, FLUOROPOLYMER AND METHOD FOR PRODUCING THE COMPOUND

TECHNICAL FIELD

The present invention relates to a novel fluorinated compound, a fluoropolymer and a method for producing the compound.

BACKGROUND ART

A fluoropolymer containing repeating units having a fluorinated alicyclic structure in its main chain is excellent in physical properties such as optical characteristics (such as transparency and durable light resistance) and water and oil repellency.

As a cyclic polymerizable compound which forms the above repeating units, a polyfluoroalkenyl vinyl ether such as $CF_2=CFOCF_2CF_2CF=CF_2$ has been known (e.g. Patent Document 1).

Further, a fluoropolymer containing repeating units having a fluorinated alicyclic structure in its main chain and having a functional group is excellent in the above physical properties and in addition, physical properties derived from the above functional group can be developed, and such a polymer is applied to various fields (e.g. a resist material for lithography) (e.g. Patent Document 2).

As a cyclic polymerizable compound which forms the above repeating units, Patent Document 2 discloses a fluoroalkadiene having a functional group (such as $CF_2=CFCF_2C(CF_3)(OH)CH_2CH=CH_2$).

Further, as a fluoroalkadiene having a group analogues to a carboxyl group, Patent Document 3 discloses 1,1,2-trifluoro-4-alkoxycarbonyl-1,6-heptadiene ($CF_2=CFCH_2CH(C(O)OC(CH_3)_3)CH_2CH=CH_2$ or the like).

Patent Document 1: JP-A-01-131215
Patent Document 2: WO02/064648
Patent Document 3: JP-A-2005-298707

DISCLOSURE OF THE INVENTION

Problems to be Solved by the Invention

As a fluoroalkadiene having a functional group, compounds having various structures have been desired depending on the purpose of use of the resulting polymer. However, even if such a compound is to be obtained in practice, it is difficult to obtain material compounds in many cases, and such a compound is not necessarily easily obtained.

Further, also with respect to a fluoroalkadiene having a group analogues to a carboxyl group, only the above compound as disclosed in Patent Document 3 has been known, and no other compounds have been known.

Means to Solve the Problems

The present invention has been made to solve the above problems and provides a novel fluoroalkadiene having a carboxyl group or a group analogues thereto, such as 1,1,2,3,3-pentafluoro-4-alkoxycarbonyl-1,6-heptadiene, a polymer thereof and a method for producing the compound.

That is, the present invention provides the following.

1. A compound represented by the following formula (1):

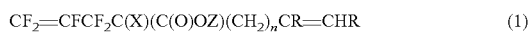

wherein X is a hydrogen atom, a cyano group or a group represented by the formula —C(O)OZ; Z is a hydrogen atom or a $C_{1-20}$ monovalent organic group; n is 0, 1 or 2; and R is a hydrogen atom or a $C_{1-20}$ monovalent organic group, provided that two R's may be the same or different.

2. A compound represented by the following formula (11):

wherein $Z^1$ is a hydrogen atom, a group represented by the formula —$C(Y^1)_3$, a group represented by the formula —$CH_2OY^2$ or a group represented by the following formula:

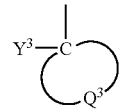

each of $Y^1$ and $Y^2$ which are independent of each other, is a hydrogen atom or a $C_{1-19}$ monovalent saturated hydrocarbon group; $Y^3$ is a hydrogen atom or a $C_{1-16}$ monovalent saturated hydrocarbon group; and $Q^3$ is a $C_{3-19}$ group which forms a bivalent cyclic hydrocarbon group in combination with the carbon atom in the formula, provided that in $Y^1$, $Y^2$ and $Y^3$ in the case of a monovalent saturated hydrocarbon group and $Q^3$, between the carbon atom-carbon atom, a group represented by the formula —O—, a group represented by the formula —C(O)— or a group represented by the formula —C(O)O— may be inserted, and to a carbon atom in $Y^1$, $Y^2$, $Y^3$ and $Q^3$, a fluorine atom, a hydroxyl group or a carboxyl group may be bonded.

3. A compound represented by the following formula (111):

wherein $Z^{11}$ is a hydrogen atom, a group represented by the formula —$C(Y^{11})_3$, a group represented by the formula —$CH_2OY^{21}$ or a group represented by the formula:

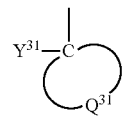

$Y^{11}$ is a $C_{1-6}$ monovalent saturated hydrocarbon group, $Y^{21}$ is a $C_{1-12}$ monovalent saturated hydrocarbon group or a $C_{2-12}$ monovalent saturated hydrocarbon group containing a group represented by the formula —O—; $Y^{31}$ is a hydrogen atom or a $C_{1-6}$ monovalent saturated hydrocarbon group; and $Q^{31}$ is a $C_{4-12}$ a bivalent saturated hydrocarbon group, a $C_{4-12}$ bivalent fluorinated saturated hydrocarbon group or a $C_{4-12}$ bivalent saturated hydrocarbon group having a group represented by the formula —O—, a group represented by the formula —C(O)— or a group represented by the formula —C(O)O— inserted between the carbon atom-carbon atom.

4. A compound represented by the following formula (1111):

wherein $Z^{111}$ is a $C_{3-20}$ monovalent organic group having at least one group represented by the formula —$C(CF_3)_2OH$.

5. A compound represented by the following formula (12):

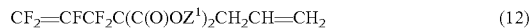

wherein $Z^1$ is a hydrogen atom, a group represented by the formula $-C(Y^1)_3$, a group represented by the formula $-CH_2OY^2$ or a group represented by the following formula:

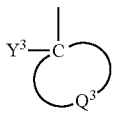

each of $Y^1$ and $Y^2$ which are independent of each other, is a hydrogen atom or a $C_{1-19}$ monovalent saturated hydrocarbon group; $Y^3$ is a hydrogen atom or a $C_{1-16}$ monovalent saturated hydrocarbon group; and $Q^3$ is a $C_{3-19}$ group which forms a bivalent cyclic hydrocarbon group in combination with the carbon atom in the formula, provided that in $Y^1$, $Y^2$ and $Y^3$ in the case of a monovalent saturated hydrocarbon group and $Q^3$, between the carbon atom-carbon atom, a group represented by the formula $-O-$, a group represented by the formula $-C(O)-$ or a group represented by the formula $-C(O)O-$ may be inserted, and to a carbon atom in $Y^1$, $Y^2$, $Y^3$ and $Q^3$, a fluorine atom, a hydroxyl group or a carboxyl group may be bonded.

6. A compound represented by the following formula (121):

$$CF_2=CFCF_2C(C(O)OZ^{11})_2CH_2CH=CH_2 \quad (121)$$

wherein $Z^{11}$ is a hydrogen atom, a group represented by the formula $-C(Y^{11})_3$, a group represented by the formula $-CH_2OY^{21}$ or a group represented by the following formula:

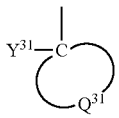

$Y^{11}$ is a $C_{1-6}$ monovalent saturated hydrocarbon group; $Y^{21}$ is a $C_{1-12}$ monovalent saturated hydrocarbon group or a $C_{2-12}$ monovalent saturated hydrocarbon group containing a group represented by the formula $-O-$; $Y^{31}$ is a hydrogen atom or a $C_{1-6}$ saturated hydrocarbon group; and $Q^{31}$ is a $C_{4-12}$ a bivalent saturated hydrocarbon group, a $C_{4-12}$ bivalent fluorinated saturated hydrocarbon group or a $C_{4-12}$ bivalent saturated hydrocarbon group having a group represented by the formula $-O-$, a group represented by the formula $-C(O)-$ or a group represented by the formula $-C(O)O-$ inserted between the carbon atom-carbon atom.

7. A method for producing a compound represented by the following formula (p12), which comprises reacting a compound represented by the following formula (p5) with a compound represented by the following formula (p4) to obtain a compound represented by the following formula (p3), and then reacting the compound with a compound represented by the following formula (p2):

$$CH_2(C(O)OZ^P)_2 \quad (p5)$$

$$CHR=CR(CH_2)_n\text{-}G^P \quad (p4)$$

$$CH(C(O)OZ^P)_2((CH_2)_nCR=CHR) \quad (p3)$$

$$CF_2=CFCF_2\text{-}J^P \quad (p2)$$

$$CF_2=CFCF_2C(C(O)OZ^P)_2(CH_2)_nCR=CHR \quad (p12)$$

wherein $Z^P$ is a $C_{1-20}$ monovalent organic group; R is a hydrogen atom or a $C_{1-20}$ monovalent organic group, provided that two R's may be the same or different; n is 0, 1 or 2; $G^P$ is a chlorine atom, a bromine atom or an iodine atom; $J^P$ is a chlorine atom, a bromine atom, an iodine atom or a group represented by the formula $-OSO_2\text{-}L^P$; and $L^P$ is a fluorine atom, a $C_{1-10}$ hydrocarbon group or a $C_{1-10}$ fluorinated hydrocarbon group.

8. A method for producing a compound represented by the following formula (12H), which comprises hydrolyzing a compound represented by the following formula (p12):

$$CF_2=CFCF_2C(C(O)OZ^P)_2(CH_2)_nCR=CHR \quad (p12)$$

$$CF_2=CFCF_2C(C(O)OH)_2(CH_2)_nCR=CHR \quad (12H)$$

wherein $Z^P$ is a $C_{1-20}$ monovalent organic group; R is a hydrogen atom or a $C_{1-20}$ monovalent organic group, provided that two R's may be the same or different; and n is 0, 1 or 2.

9. A method for producing a compound represented by the following formula (11H), which comprises decarboxylation of a compound represented by the following formula (12H):

$$CF_2=CFCF_2C(C(O)OH)_2(CH_2)_nCR=CHR \quad (12H)$$

$$CF_2=CFCF_2CH(C(O)OH)(CH_2)_nCR=CHR \quad (11H)$$

wherein R is a hydrogen atom or a $C_{1-20}$ monovalent organic group, provided that two R's may be the same or different; and n is 0, 1 or 2.

10. A method for producing a compound represented by the following formula (12W), which comprises reacting a compound represented by the following formula (12H) with a compound represented by the following formula (w):

$$CF_2=CFCF_2C(C(O)OH)_2(CH_2)_nCR=CHR \quad (12H)$$

$$CH_2=CW^P_2 \quad (w)$$

$$CF_2=CFCF_2C(C(O)OC(CH_3)W^P_2)_2(CH_2)_nCR=CHR \quad (12W)$$

wherein R is a hydrogen atom or a $C_{1-20}$ monovalent organic group, provided that two R's may be the same or different; n is 0, 1 or 2; and $W^P$ is each independently a hydrogen atom or a $C_{1-20}$ monovalent saturated hydrocarbon group, or two $W^P$'s are groups which form a $C_{3-20}$ bivalent cyclic hydrocarbon group in combination with the carbon atom in the formula.

11. A method for producing a compound represented by the following formula (11W), which comprises reacting a compound represented by the following formula (11H) with a compound represented by the following formula (w):

$$CF_2=CFCF_2CH(C(O)OH)(CH_2)_nCR=CHR \quad (11H)$$

$$CH_2=CW^P_2 \quad (w)$$

$$CF_2=CFCF_2CH(C(O)OC(CH_3)W^P_2)(CH_2)_nCR=CHR \quad (11W)$$

wherein R is a hydrogen atom or a $C_{1-20}$ monovalent organic group, provided that two R's may be the same or different; n is 0, 1 or 2; and $W^P$ is each independently a hydrogen atom or a $C_{1-20}$ monovalent saturated hydrocarbon group, or two $W^P$'s are groups which form a $C_{3-20}$ bivalent cyclic hydrocarbon group in combination with the carbon atom in the formula.

12. A polymer obtained by polymerizing a compound represented by the formula (1).

13. A polymer obtained by polymerizing a compound represented by the following formula (2):

$$CF_2=CFCF_2CH(C(O)OZ^{111})(CH_2)_nCR=CHR \qquad (2)$$

wherein $Z^{111}$ is a $C_{3\text{-}20}$ monovalent organic group having at least one group represented by the formula $-C(CF_3)_2OH$; n is 0, 1 or 2; and R is a hydrogen atom or a $C_{1\text{-}20}$ monovalent organic group, provided that two R's may be the same or different.

14. The polymer according to the above 12 or 13, which has a weight average molecular weight of from 1,000 to 1,000,000.

EFFECTS OF THE INVENTION

According to the present invention, a cyclic polymerizable compound to form repeating units having a fluorinated alicyclic structure in its main chain and having a carboxyl group or a group analogues thereto, is provided. The polymer of the present invention has a high fluorine content and is thereby particularly excellent in water and oil repellency and optical characteristics (such as transparency and durable light resistance).

BEST MODE FOR CARRYING OUT THE INVENTION

In the present specification, a compound represented by the formula (1) will sometimes be referred to as a compound (1), and a group represented by the formula $-C(Y^1)_3$ will be referred to as $-C(Y^1)_3$. The same applies to other compounds and other groups. Further, symbols in groups are as defined above unless otherwise specified.

The present invention provides the following compound (1):

$$CF_2=CFCF_2C(X)(C(O)OZ)(CH_2)_nCR=CHR \qquad (1)$$

In the compound (1), X is a hydrogen atom, a cyano group or a formula $-C(O)OZ$. Among them, X is preferably a hydrogen atom or $-C(O)OZ$.

In the compound (1), Z is a hydrogen atom or a $C_{1\text{-}20}$ monovalent organic group. Among them, Z is preferably $Z^1$. This $Z^1$ is a hydrogen atom, $-C(Y^1)_3$ (hereinafter sometimes referred to as a group (Y1)), $-CH_2OY^2$ (hereinafter sometimes referred to as a group (Y2)) or a group represented by the following formula (hereinafter sometimes referred to as a group (Y3) and sometimes abbreviated as $-C(Y^3)(=Q^3)$):

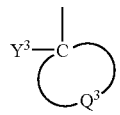

Further, Z is more preferably $Z^{11}$. This $Z^{11}$ is a hydrogen atom, $-C(Y^{11})_3$, $-CH_2OY^{21}$ or $-C(Y^{31})(=Q^{31})$. Further, Z is also preferably a group ($Z^{111}$) having at least one group represented by the formula $-C(CF_3)_2OH$ (bistrifluoromethylcarbinol group).

Each of $Y^1$, $Y^2$ and $Y^3$ which are independent of one another, in a case where they are not a hydrogen atom, may be a non-cyclic group or may be a group containing a cyclic group. The non-cyclic group may be a linear group or may be a branched group. The group containing a cyclic group may be a group containing a polycyclic group or may be a group containing a monocyclic group. The group containing a polycyclic group may be a group containing a bridged cyclic group or may be a group containing a condensed cyclic group.

As specific examples of the group containing a cyclic group, a group containing each of the following groups or a group having a hydrogen atom in such a group substituted by a fluorine atom may be mentioned.

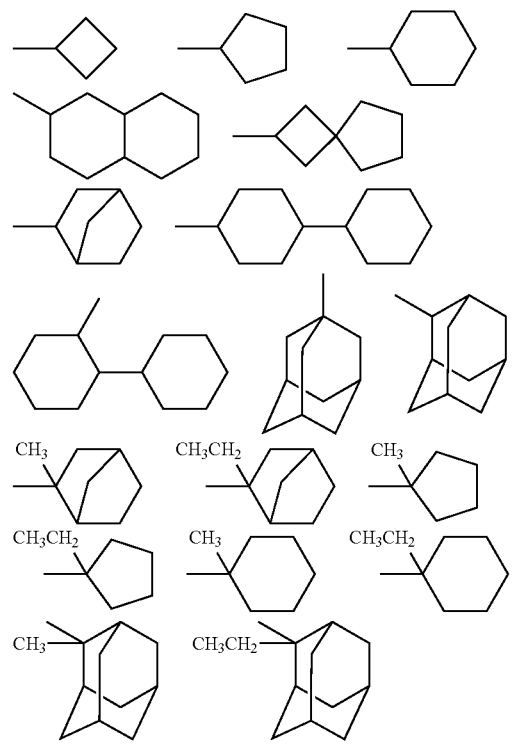

As specific examples of the group having a hydrogen atom in the group containing a cyclic group substituted by a fluorine atom, the following groups may be mentioned.

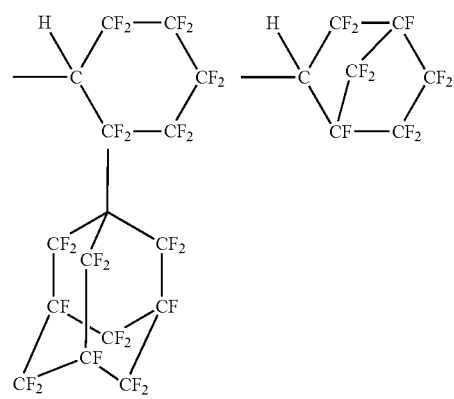

In the group (Y1), the three $Y^1$'s may be the same or different.

Each of the three $Y^1$'s is a hydrogen atom or a $C_{1\text{-}19}$ monovalent saturated hydrocarbon group. Further, in $Y^1$ in the case of a monovalent saturated hydrocarbon group, between the carbon atom-carbon atom, a group represented by the formula —O— (etheric oxygen atom), a group represented by the formula —C(O)— (carbonyl group) or a group represented by the formula —C(O)O— (ester group) may be inserted. Further, to a carbon atom in $Y^1$, a fluorine atom, a hydroxyl group or a carboxyl group may be bonded. Further, $Y^1$ preferably has at least one bistrifluoromethylcarbinol group.

The three $Y^1$'s are preferably such a combination that two are $C_{1-6}$ monovalent saturated hydrocarbon groups and one is a $C_{1-12}$ monovalent cyclic saturated hydrocarbon group, such a combination that two are hydrogen atoms and one is a $C_{1-12}$ polyfluoroalkyl group, or such a combination that three are $C_{1-6}$ monovalent saturated hydrocarbon groups ($Y^{11}$). Further, three $Y^1$'s are particularly preferably such a combination that two are $C_{1-6}$ alkyl groups (preferably a methyl group) and one is a 1-adamantyl group, such a combination that they are polyfluoroalkyl groups represented by the formula —$CH_2R^{FY}$ (wherein $R^{FY}$ is a $C_{1-10}$ perfluoroalkyl group), or such a combination that three are $C_{1-6}$ alkyl groups (preferably a methyl group).

$Y^2$ in the group (Y2) is a hydrogen atom or a $C_{1-19}$ monovalent saturated hydrocarbon group, provided that in $Y^2$ in the case of a monovalent saturated hydrocarbon group, between the carbon atom-carbon atom, a group represented by the formula —O—, a group represented by the formula —C(O)— or a group represented by the formula —C(O)O— may be inserted. Further, to a carbon atom in $Y^2$, a fluorine atom, a hydroxyl group or a carboxyl group may be bonded. Further, $Y^2$ preferably has at least one bistrifluoromethylcarbinol group.

$Y^2$ is preferably a $C_{1-12}$ monovalent saturated hydrocarbon group, a $C_{2-12}$ monovalent saturated hydrocarbon group containing —O—, a $C_{1-12}$ monovalent fluorinated saturated hydrocarbon group or a $C_{2-12}$ monovalent fluorinated saturated hydrocarbon group containing —O—. Among them, $Y^2$ is more preferably $Y^{21}$ (a $C_{1-12}$ monovalent saturated hydrocarbon group or a $C_{2-12}$ monovalent saturated hydrocarbon group containing —O—).

As specific examples of the group (Y2), the following groups may be mentioned.

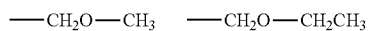

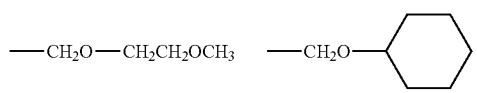

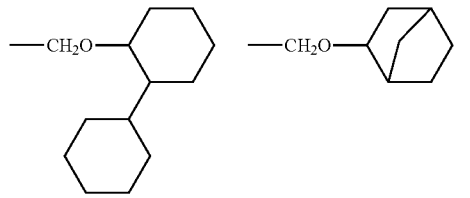

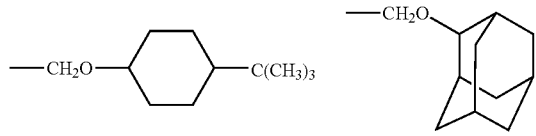

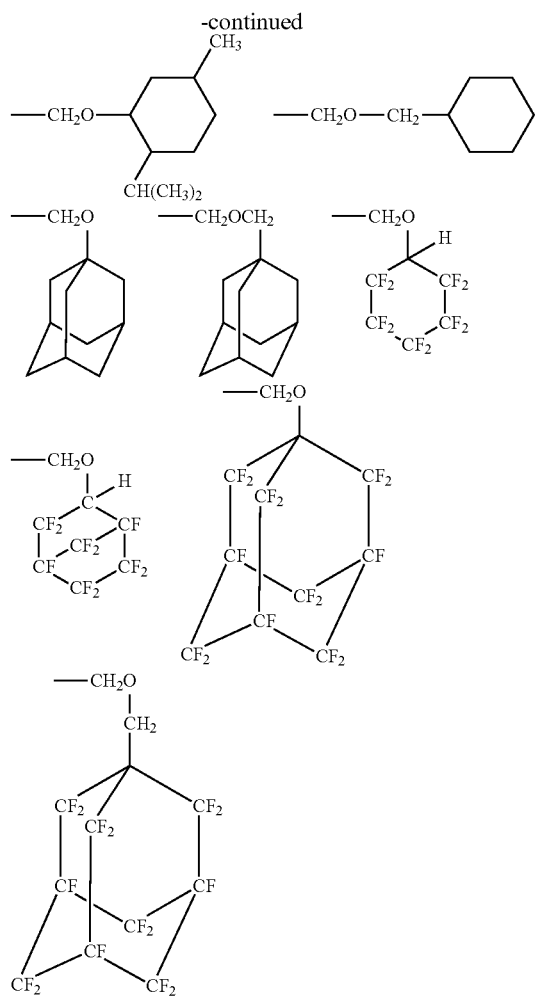

$Y^3$ in the group (Y3) is a hydrogen atom or a $C_{1-16}$ monovalent saturated hydrocarbon group, provided that in $Y^3$ in the case of a monovalent saturated hydrocarbon group, between the carbon atom-carbon atom, a group represented by the formula —O—, a group represented by the formula —C(O)— or a group represented by the formula —C(O)O— may be inserted. Further, to a carbon atom in $Y^3$, a fluorine atom, a hydroxyl group or a carboxyl group may be bonded. Further, $Y^3$ preferably has at least one bistrifluoromethylcarbinol group.

$Y^3$ is preferably a hydrogen atom, a $C_{1-6}$ monovalent saturated hydrocarbon group or a $C_{2-6}$ monovalent saturated hydrocarbon group containing —O—. Among them, $Y^3$ is more preferably $Y^{31}$ (a hydrogen atom or a $C_{1-6}$ monovalent saturated hydrocarbon group).

$Q^3$ in the group (Y3) is a $C_{3-19}$ group which forms a bivalent cyclic hydrocarbon group in combination with the carbon atom in the formula, provided that between the carbon atom-carbon atom in $Q^3$, a group represented by the formula —O—, a group represented by the formula —C(O)— or a group represented by the formula —C(O)O— may be inserted. Further, to a carbon atom in $Q^3$, a fluorine atom, a hydroxyl group or a carboxyl group may be bonded. Further, $Q^3$ preferably has at least one bistrifluoromethylcarbinol group.

$Q^3$ may be a group which forms a bivalent monocyclic hydrocarbon group in combination with the carbon atom in the formula or may be a group which forms a bivalent polycyclic hydrocarbon group in combination with the carbon atom in the formula. The polycyclic hydrocarbon group may be a condensed cyclic hydrocarbon group or may be a bridged cyclic hydrocarbon group. $Q^3$ is preferably a saturated group.

$Q^3$ is preferably a $C_{4-12}$ bivalent saturated hydrocarbon group, a $C_{4-12}$ bivalent saturated hydrocarbon group having —O—, —C(O)— or —C(O)O— inserted between the carbon atom-carbon atom, a $C_{4-12}$ bivalent fluorinated saturated hydrocarbon group or a $C_{4-12}$ bivalent fluorinated saturated hydrocarbon group having —O—, —C(O)— or —C(O)O— inserted between the carbon atom-carbon atom. Among them, $Q^3$ is more preferably $Q^{31}$ (a $C_{4-12}$ bivalent saturated hydrocarbon group, a $C_{4-12}$ bivalent fluorinated saturated hydrocarbon group or a $C_{4-12}$ bivalent saturated hydrocarbon group having —O—, —C(O)— or —C(O)O— inserted between the carbon atom-carbon atom).

As specific example of the group (Y3), groups represented by the following formulae may be mentioned.

In the compound (1), n is 0, 1 or 2, preferably 1.

In the compound (1), R is a hydrogen atom or a $C_{1-20}$ monovalent organic group, provided that two R's may be the same or different. It is preferred that both the two R's are hydrogen atoms.

R which is a $C_{1-20}$, preferably $C_{1-12}$ monovalent organic group, is preferably a $C_{1-12}$ monovalent saturated hydrocarbon group. The monovalent saturated hydrocarbon group may be a non-cyclic group or may be a cyclic group. The non-cyclic group may be a linear group or may be a branched group. The cyclic group may be a polycyclic group or may be a mono group. The polycyclic group may be a bridged cyclic group or may be a condensed cyclic group.

In the monovalent saturated hydrocarbon group as R, between the carbon atom-carbon atom, —O— may be inserted. Further, to a carbon atom in the monovalent saturated hydrocarbon group, a fluorine atom, a hydroxyl group or a carboxyl group may be bonded.

The compound (1) is preferably the following compound (11) or the following compound (12):

$$CF_2\!\!=\!\!CFCF_2CH(C(O)OZ^1)CH_2CH\!\!=\!\!CH_2 \qquad (11)$$

$$CF_2\!\!=\!\!CFCF_2C(C(O)OZ^1)_2CH_2CH\!\!=\!\!CH_2 \qquad (12)$$

Further, the compound (11) is preferably the following compound (111), and the compound (12) is preferably the following compound (121):

$$CF_2\!\!=\!\!CFCF_2CH(C(O)OZ^{11})CH_2CH\!\!=\!\!CH_2 \qquad (111)$$

$$CF_2\!\!=\!\!CFCF_2C(C(O)OZ^{11})_2CH_2CH\!\!=\!\!CH_2 \qquad (121)$$

Further, the compound (1) is preferably the following compound (2), particularly preferably the compound (1111):

$$CF_2\!\!=\!\!CFCF_2CH(C(O)OZ^{111})(CH_2)_nCR\!\!=\!\!CHR \qquad (2)$$

$$CF_2\!\!=\!\!CFCF_2CH(C(O)OZ^{111})CH_2CH\!\!=\!\!CH_2 \qquad (1111)$$

As specific examples of the compound (1), the following compounds may be mentioned. Specific examples of the compound (1) wherein Z is a hydrogen atom: $CF_2\!\!=\!\!CFCF_2CH(C(O)OH)CH_2CH\!\!=\!\!CH_2CF_2\!\!=\!\!CFCF_2C(C(O)OH)_2CH_2CH\!\!=\!\!CH_2CF_2\!\!=\!\!CFCF_2C(CN)(C(O)OH)CH_2CH\!\!=\!\!CH_2$ Specific examples of the compound (1) wherein Z is the group (Y1): $CF_2\!\!=\!\!CFCF_2CH(C(O)OC(CH_3)_3)CH_2CH\!\!=\!\!CH_2CF_2\!\!=\!\!CFCF_2C(C(O)OC(CH_3)_3)_2CH_2CH\!\!=\!\!CH_2CF_2\!\!=\!\!CFCF_2CH(C(O)O(CH_2)_3C(CF_3)OH)CH_2CH\!\!=\!\!CH_2CF_2\!\!=\!\!CFCF_2CH(C(O)OCH(CH_3)C(CF_3)_2OH)CH_2CH\!\!=\!\!CH_2CF_2\!\!=\!\!CFCF_2CH(C(O)OCH(CH_2C(CF_3)_2OH)_2)CH_2CH\!\!=\!\!CH_2CF_2\!\!-\!\!CFCF_2C(CN)(C(O)OC(CH_3)_3)CH_2CH\!\!=\!\!CH_2CF_2\!\!=\!\!CFCF_2CH(C(O)OCH_2CF_2CF_3)CH_2CH\!\!=\!\!CH_2$ Specific examples of the compound (1) wherein Z is the group (Y2):

$$CF_2\!\!=\!\!CFCF_2CH(C(O)OCH_2OCH_3)CH_2CH\!\!=\!\!CH_2$$

$$CF_2\!\!=\!\!CFCF_2CH(C(O)OCH_2OCH_2CH_3)CH_2CH\!\!=\!\!CH_2$$

$$CF_2\!\!=\!\!CFCF_2C(C(O)OCH_2OCH_3)_2CH_2CH\!\!=\!\!CH_2$$

$$CF_2\!\!=\!\!CFCF_2C(CN)(C(O)OCH_2OCH_3)CH_2CH\!\!=\!\!CH_2$$

$$CF_2\!\!=\!\!CFCF_2CH(C(O)OCH_2OCH_2CH_2OCH_3)CH_2CH\!\!=\!\!CH_2$$

$$CF_2\!\!=\!\!CFCF_2CHCH_2CH\!\!=\!\!CH_2$$
$$|$$
$$C(O)OCH_2OCH_2$$
(adamantyl)

$$CF_2\!\!=\!\!CFCF_2CHCH_2CH\!\!=\!\!CH_2$$
$$|$$
$$C(O)OCH_2O$$
(adamantyl)

$$CF_2\!\!=\!\!CFCF_2CHCH_2CH\!\!=\!\!CH_2$$
$$|$$
$$C(O)OCH_2O$$
(bicyclohexyl)

Specific examples of the compound (1) wherein Z is the group (Y3):

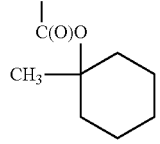

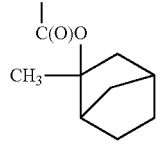

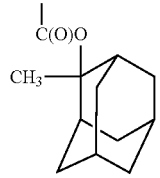

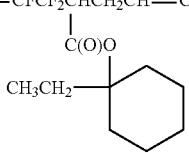

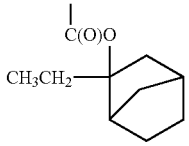

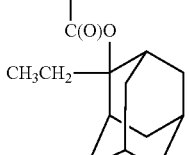

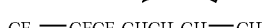
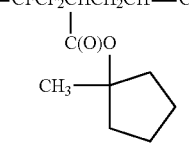

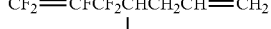
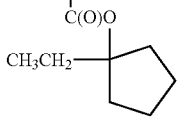

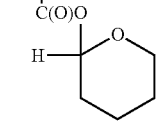

-continued

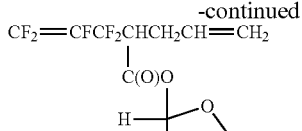
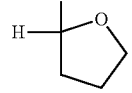

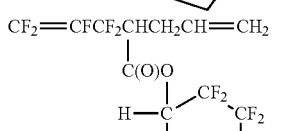
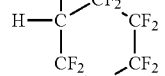

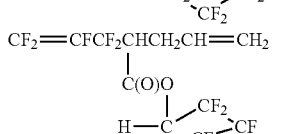
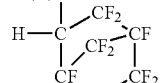

The present invention provides a method for producing the following compound (p12), which comprises reacting the following compound (p5) with the following compound (p4) to obtain the following compound (p3), and then reacting the compound (p3) with the following compound (p2):

$$CH_2(C(O)OZ^P)_2 \quad (p5)$$

$$CHR=CR(CH_2)_n\text{-}G^P \quad (p4)$$

$$CH(C(O)OZ^P)_2((CH_2)_nCR=CHR) \quad (p3)$$

$$CF_2=CFCF_2\text{-}J^P \quad (p2)$$

$$CF_2=CFCF_2C(C(O)OZ^P)_2(CH_2)_nCR=CHR \quad (p12)$$

$Z^P$ is a $C_{1-20}$ monovalent organic group. $Z^P$ is preferably a $C_{1-20}$ monovalent saturated hydrocarbon group which may contain —O—, —C(O)— or —C(O)O—. Further, $Z^P$ is particularly preferably a $C_{1-6}$ alkyl group.

R and n are as defined above.

$G^P$ is a chlorine atom, a bromine atom or an iodine atom, preferably a chorine atom or a bromine atom.

$J^P$ is a chlorine atom, a bromine atom, an iodine atom or a group represented by the formula —OSO$_2$-L$^P$. Further, L$^P$ is a fluorine atom, a $C_{1-10}$ hydrocarbon group or a $C_{1-10}$ fluorinated hydrocarbon group. L$^P$ in J$^P$ is preferably a fluorine atom, a methyl group, a trifluoromethyl group or a 4-methylphenyl group, particularly preferably a fluorine atom.

The reaction of the compound (p5) with the compound (p4) is carried out preferably in the presence of a basic compound. The basic compound is not particularly limited and is preferably a metal hydride, particularly preferably NaH, NaBH$_4$ or LiAlH$_4$.

The above reaction is carried out preferably in the presence of an aprotic solvent. The aprotic solvent may, for example, be specifically diethyl ether, methyl tert-butyl ether, tetrahydrofuran, dioxane, monoglyme, diglyme, triglyme, tetraglyme, acetonitrile, benzonitrile, sulfolane, dimethylformamide, dimethylacetamide or dimethylsulfoxide.

The reaction temperature is not particularly limited and is preferably from −78° C. to +25° C. The reaction pressure is not particularly limited.

The reaction of the compound (p3) with the compound (p2) is carried out preferably in the presence of a basic compound. Further, the reaction is carried out preferably in the presence of an aprotic solvent. The reaction temperature is not particularly limited and is preferably from −78° C. to +25° C. The reaction pressure is not particularly limited. Further, specific examples of the basic compound and specific examples of the aprotic solvent are the same as those in the reaction of the compound (p5) with the compound (p4).

As specific examples of the compound (p5), $CH_2(C(O)OCH_3)_2$, $CH_2(C(O)OCH_2CH_3)_2$, $CH_2(C(O)OC(Y^1)_3)_2$, $CH_2(C(O)OCH_2OY^2)_2$ and the following compound may be mentioned. $Y^1$ and $Y^2$ are as defined above.

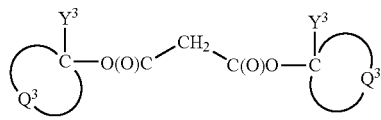

As specific examples of the compound (p4), $CH_2\!=\!CHCH_2Cl$, $CH_2\!=\!CHCH_2Br$, $CH_2\!=\!CHCH_2CH_2Cl$ and $CH_2\!=\!CHCH_2CH_2Br$ may be mentioned.

As specific examples of the compound (p3), $CH(C(O)OCH_3)_2(CH_2CH\!=\!CH_2)$, $CH(C(O)OCH_2CH_3)_2(CH_2CH\!=\!CH_2)$, $CH(C(O)OC(Y^1)_3)_2(CH_2CH\!=\!CH_2)$, $CH(C(O)OCH_2OY^2)_2(CH_2CH\!=\!CH_2)$ and the following compound may be mentioned.

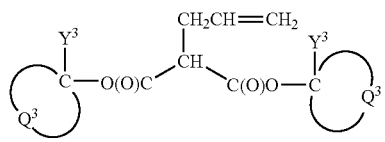

As specific examples of the compound (p2), $CF_2\!=\!CFCF_2OSO_2F$ may be mentioned.

As specific examples of the compound (p12), $CF_2\!=\!CFCF_2C(C(O)OCH_3)_2CH_2CH\!=\!CH_2$, $CF_2\!=\!CFCF_2C(C(O)OCH_2CH_3)_2CH_2CH\!=\!CH_2$, $CF_2\!=\!CFCF_2C(C(O)OC(Y^1)_3)_2CH_2CH\!=\!CH_2$, $CF_2\!=\!CFCF_2C(C(O)OCH_2OY^2)_2CH_2CH\!=\!CH_2$ and the following compound may be mentioned:

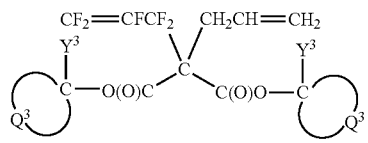

Further, the compound (p12) may be prepared by reacting the compound (p5) with the compound (p2) to obtain the following compound (p3F), and then reacting the compound (p3F) with the compound (p4):

$$CH(C(O)OZ^P)_2(CF_2CF\!=\!CF_2) \quad (p3F)$$

The present invention provides a method for producing the following compound (12H), which comprises hydrolyzing the compound (p12):

$$CF_2\!=\!CFCF_2C(C(O)OH)_2(CH_2)_nCR\!=\!CHR \quad (12H)$$

The hydrolysis of the compound (p12) is carried out preferably under acidic conditions, particularly preferably in the presence of a protic acid. The protic acid may be an inorganic acid or may be an organic acid. As specific examples of the protic acid, a carboxylic acid and a sulfonic acid may be mentioned.

Further, the hydrolysis may be carried out in the presence of a solvent or may be carried out in the absence of a solvent. The temperature at the hydrolysis is not particularly limited and is preferably from −78° C. to +25° C. The reaction pressure is not particularly limited.

The present invention provides a method for producing the following compound (11H) which comprises decarboxylation of the compound (12H):

$$CF_2\!=\!CFCF_2CH(C(O)OH)(CH_2)_nCR\!=\!CHR \quad (11H)$$

The decarboxylation of the compound (12H) is carried out preferably by heating the compound (12H). The temperature at the time of heating the compound (12H) is preferably from 50 to 200° C. Further, the pressure at the time of heating the compound (12H) is not particularly limited.

The present invention provides a method for producing the following compound (12W), which comprises reacting the compound (12H) with the following compound (w), and a method for producing the following compound (11W), which comprises reacting the compound (11H) with the following compound (w):

$$CR^1R^2\!=\!CW^P{}_2 \quad (w)$$

$$CF_2\!=\!CFCF_2C(C(O)OC(CH_3)W^P{}_2)_2(CH_2)_n CR\!=\!CHR \quad (12W)$$

$$CF_2\!=\!CFCF_2CH(C(O)OC(CH_3)W^P{}_2)(CH_2)_n CR\!=\!CHR \quad (11W)$$

In the above, each of $R^1$ and $R^2$ which may be the same or different, is a hydrogen atom or a $C_{1\text{-}20}$, preferably $C_{1\text{-}12}$ monovalent organic group. Each of $R^1$ and $R^2$ is preferably a $C_{1\text{-}12}$ monovalent saturated hydrocarbon group. The monovalent saturated hydrocarbon group may be a non-cyclic group or may be a cyclic group. The non-cyclic group may be a linear group or may be a branched group. The cyclic group may be a polycyclic group or may be a monocyclic group. The polycyclic group may be a bridged cyclic group or may be a condensed cyclic group. Between the carbon atom-carbon atom in the monovalent saturated hydrocarbon group, —O— may be inserted. Further, to a carbon atom in the monovalent saturated hydrocarbon group, a fluorine atom, a hydroxyl group or a carboxyl group may be bonded. Further, it may have a bistrifluoromethylcarbinol group.

The respective reactions are carried out preferably under acidic conditions. The temperature and the pressure in the respective reactions are not particularly limited.

As specific examples of the compound (w), the following compounds may be mentioned:

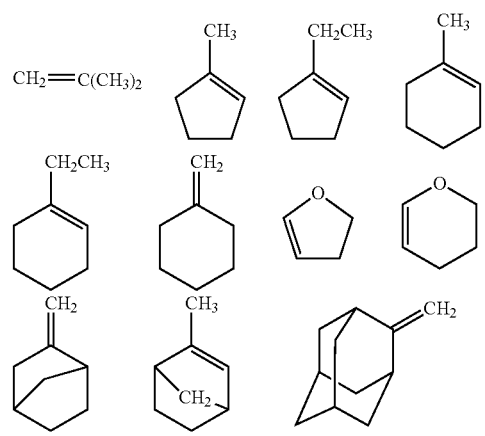

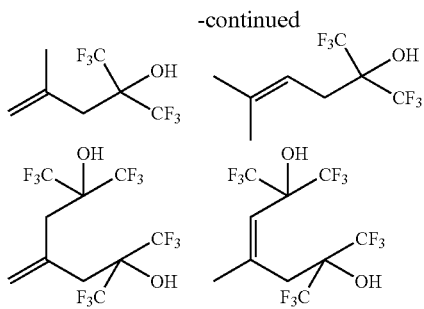

Further, the following compound (p12) or the following compound (p11) may be produced by reacting the compound (12H) or the compound (11H) with $Z^P$-OH or $Z^P$-Cl under acidic conditions:

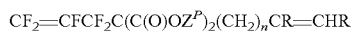

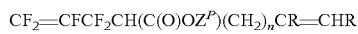

Further, in a case where $Z^P$-OH is used, the carboxyl group in the compound (12H) or (11H) is preferably activated by an activating agent such as dicyclohexylcarbodiimide.

As specific examples of the compound $Z^P$-OH, the following compounds may be mentioned.

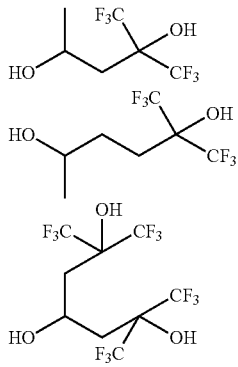

The compound (1) of the present invention is a 1,1,2,3,3-pentafluoro-4-carboxy-alkadiene not known in any literature, and is useful as a polymerizable compound.

The present invention provides a polymer obtained by polymerizing the compound (1) (hereinafter sometimes referred to as a polymer of the present invention). The compound (1) is a cyclic polymerizable compound, and the polymer of the present invention is usually a fluoropolymer containing at least one type of repeating units (U) selected from the group consisting of repeating units represented by the following formulae (U1), (U2) and (U3):

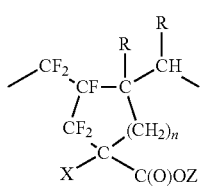

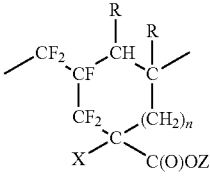

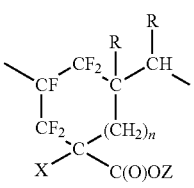

The weight average molecular weight of the polymer of the present invention is not particularly limited and is preferably from 1,000 to 1,000,000.

Polymerization of the compound (1) is carried out preferably in the presence of a polymerization initiator.

The polymerization initiator is preferably a radical polymerization initiator, more preferably a peroxide, an azo compound or a persulfate, particularly preferably a peroxide.

As specific examples of the peroxide, $C_6H_5C(O)OOC(O)C_6H_5$, $C_6F_5C(O)OOC(O)C_6F_5$, $CF_3CF_2CF_2C(O)OOC(O)CF_2CF_2CF_3$, $(CH_3)_3CC(O)OOC(O)C(CH_3)_3$, $(CH_3)_2CHC(O)OOC(O)CH(CH_3)_2$, $(CH_3)_3CC_6H_{10}C(O)OOC(O)C_6H_{10}C(CH_3)_3$, $(CH_3)_3COC(O)OOC(O)OC(CH_3)_3$, $(CH_3)_2CHOC(O)OOC(O)OCH(CH_3)_2$ and $(CH_3)_3CC_6H_{10}OC(O)OOC(O)OC_6H_{10}C(CH_3)_3$ may be mentioned (wherein $C_6H_5$ is a phenyl group, $C_6F_5$ is a pentafluorophenyl group and $C_6H_{10}$ is a 1,4-cyclohexylene group).

The method for polymerizing the compound (1) is not particularly limited, and is carried out preferably in accordance with a polymerization method such as a bulk polymerization method, a solution polymerization method, a suspension polymerization method or an emulsion polymerization method.

In a case where a polymerization solvent is used for polymerization of the compound (1), the type of the polymerization solvent is not particularly limited.

As specific examples of the polymerization solvent, aliphatic hydrocarbons such as pentane, hexane and heptane; hydrocarbon alcohols such as methanol, ethanol, n-propanol, isopropanol and tert-butanol; hydrocarbon ketones such as acetone, methyl ethyl ketone, methyl isobutyl ketone and cyclohexanone; hydrocarbon ethers such as dimethyl ether, diethyl ether, methyl ethyl ether, methyl tert-butyl ether, diethylene glycol dimethyl ether and tetraethylene glycol dimethyl ether; alicyclic hydrocarbon ethers such as tetrahydrofuran and 1,4-dioxane; nitriles such as acetonitrile; hydrocarbon esters such as methyl acetate, ethyl acetate, propyl acetate, isopropyl acetate, butyl acetate, tert-butyl acetate, methyl propionate and ethyl propionate; aromatic hydrocarbons such as toluene and xylene; chlorinated hydrocarbons such as methylene chloride, chloroform and carbon tetrachloride; chlorofluorohydrocarbons such as R-113, R-113a, R-141b, R-225ca and R225-cb; fluorinated hydrocarbons such as 1,1,1,2,2,3,3,4,4,5,5,6,6-tridecafluorohexane and 1,1,1,2,2,3,3,4,4-nonafluorohexane; fluorinated hydrocarbon ethers such as methyl 2,2,3,3-tetrafluoroethyl ether; and fluorinated hydrocarbon alcohols such as 2,2,2-trifluoroethanol, 1,1,1,3,3,3-hexafluoroisopropanol, 2,2,3,3-tetrafluoropropanol and 2,2,3,3,4,4,5,5-octafluoropentanol may be mentioned.

The temperature and the pressure in the polymerization of the compound (1) are not particularly limited. The polymerization temperature is preferably from 0° C. to 200° C., particularly preferably from 25° C. to 100° C. The polymerization pressure is preferably from the atmospheric pressure to 100 atm, particularly preferably from the atmospheric pressure to 10 atm.

The polymer of the present invention may be a homopolymer comprising the repeating units (U) alone or may be a copolymer containing the repeating units (U) and repeating units other than the repeating units (U). The copolymer is produced preferably by copolymerizing the compound (1) with a polymerizable compound other than the compound (1) (hereinafter referred to as other compound).

Said other compound is not particularly limited so long as it is a polymerizable compound copolymerizable with the compound (1).

As said other compound, α-olefins such as ethylene, propylene and isobutylene; fluorinated olefins such as tetrafluoroethylene, hexafluoropropylene, perfluoro(2,2-dimethyl-1,3-dioxole and perfluoro(butenyl vinyl ether); aftermentioned hydrofluorodienes; vinyl esters such as (meth) acrylic acid, a (meth)acrylate, vinyl acetate, vinyl benzoate and vinyl adamantate; vinyl ethers such as ethyl vinyl ether and cyclohexyl vinyl ether; cyclic olefins such as cyclohexene, norbornene and norbornadiene; maleic anhydride and vinyl chloride may be mentioned. Here, (meth)acrylic acid means acrylic acid and methacrylic acid, and the (meth)acrylate means an acrylate and a methacrylate.

Said other compound is preferably a fluorodiene or a (meth)acrylate, particularly preferably $CF_2=CF-Q^M-CH=CH_2$, $CH_2=CHC(O)OZ$ or $CH_2=C(CH_3)C(O)OZ$ (wherein $Q^M$ is $-CF_2C(CF_3)(OZ)CH_2-$, $-CH_2CH(CF_3)_2(OZ)CH_2-$ or $-CH_2CH(C(O)OZ)CH_2-$). Further, Z is a hydrogen atom or a $C_{1-20}$ monovalent organic group as defined above.

The polymer of the present invention is a fluoropolymer containing repeating units having a fluorinated alicyclic structure in its main chain and having a carboxyl group or a group analogues thereto, derived from the repeating units (U). The carboxyl groups or groups analogues thereto in the repeating units may further be subjected to chemical exchange to produce a polymer containing other repeating units.

For example, by blocking reaction of a polymer of the compound (1) wherein Z is a hydrogen atom with a blocking agent comprising an alcohol, an alkyl halide and an alkoxyalkyl halide, a polymer having carboxyl groups in the above polymer blocked may be produced. The blocking agent may be an alcohol selected from the group consisting of HO—C(Y$^1$)$_3$, HO—CH$_2$OY$^2$ and the following compound, or an alkoxy halide of the alcohol.

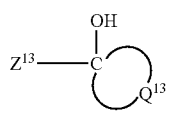

Further, as the blocking agent, an alcohol having at least 20 carbon atoms, as represented by the following formula, or its halide may be used.

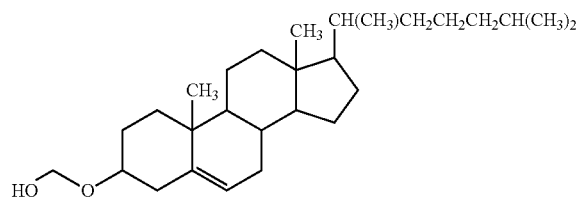

As specific examples of the blocking reaction, examples disclosed in Handbook of Reagents for Organic Synthesis: Activating Agents and Protecting Groups, edited by A. J. Pearson and W. R. Roush, John Wiley & Sons (1999) may be mentioned.

The compound (1) of the present invention is a compound having a high fluorine content as compared with a known cyclic polymerizable compound having a group analogues to a carboxyl group (1,1,2-trifluoro-4-alkoxycarbonyl-1,6-heptadiene), and is considered to be excellent in optical characteristics (such as transparency and durable light resistance) and water and oil repellency. Further, a —C(CF$_3$)$_2$OH group can easily be introduced to obtain a compound having both water and oil repellency and solubility in a developer. Accordingly, the polymer of the present invention is a material useful for an application (e.g. a material for immersion lithography) which requires optical characteristics and water and oil repellency, or optical characteristics, water and oil repellency and solubility in a developer.

EXAMPLES

Now, the present invention will be described in detail with reference to Examples. However, it should be understood that the present invention is by no means restricted thereto.

In Examples, tetrahydrofuran will be referred to as THF, dichloropentafluoropropane as R225, diisopropyl peroxydicarbonate as IPP, isopropyl alcohol as IPA, propylene glycol monomethyl ether acetate as PGMEA, tetramethylsilane as TMS, and 1,1,2-trichloro-1,2,2-trifluoroethane as R113.

Further, the weight average molecular weight of the polymer will be referred to as Mw, the number average molecular weight of the polymer as Mn, and the glass transition temperature as Tg. Mw and Mn were determined by gel permeation chromatography (developing solvent: THF, internal standard: polystyrene). Tg was measured by differential scanning calorimetry.

Example 1

Example for Preparation of Compound (1)

Example 1-1

Example for Preparation of $CF_2=CFCF_2C(C(O)OC(CH_3)_3)_2CH_2CH=CH_2$ (Hereinafter Referred to as a Compound ($12^1$))

In a reactor, NaH (2.1 g) with a purity of 60% and THF (100 mL) were added. $CH_2(C(O)OC(CH_3)_3)_2$ was dropwise added at 25° C. over a period of 20 minutes with mixing and stirring. After completion of the dropwise addition, the content in the reactor was stirred at 25° C. as it was for 100 minutes. Further, $CH_2=CHCH_2Br$ (6.0 g) was added to the reactor over a period of 10 minutes, and the content in the reactor was stirred at 65° C. for 5 hours. Then, water (100 mL) was added to the reactor to quench the reaction. The liquid in the reactor was subjected to extraction with 50 mL of tert-butyl methyl ether three times. The extract was washed with a salt solution and then dried over sodium sulfate. The extract was further concentrated and then distilled under reduced pressure to obtain $CH_2$=$CHCH_2CH(C(O)OC(CH_3)_3)_2$ (9.4 g) with a NMR purity of 90%.

To the reactor, NaH (1.8 g) with a purity of 60% and THF (80 mL) were put. To the reactor, $CH_2$=$CHCH_2CH(C(O)OC(CH_3)_3)_2$ (9.4 g) was dropwise added over a period of 15 minutes with mixing and stirring. At the time of dropwise addition, the internal temperature of the reactor was kept at 20° C. or below. The content in the reactor was stirred at 25° C. as it is for 75 minutes.

Then, at an internal temperature of the reactor of 0° C., $CF_2$=$CFCF_2OSO_2F$ (8.5 g) was added to the reactor over a period of 25 minutes. The liquid in the reactor was yellowed and a solid material ($FSO_3Na$) was precipitated. The content in the reactor was stirred as it was for 20 hours. Water (150 mL) was added to the reactor to quench the reaction.

The solution in the reactor was subjected to extraction with tert-butyl methyl ether (50 mL) three times. The extract was washed with a sodium chloride aqueous solution, dried over sodium sulfate and concentrated to obtain a crude product. The crude product was purified by silica gel column chromatography to obtain a compound $(12^1)$ (5.3 g).

The NMR data and IR data of the compound $(12^1)$ are shown below.

$^1$H-NMR (300.4 MHz, solvent: $CDCl_3$, standard: TMS) δ (ppm): 1.47 (s, 18H), 2.85 (d, J=6.9 Hz, 2H), 5.11 (dm, J=10.3 Hz, 1H), 5.18 (dm, J=17.1 Hz, 1H), 5.90 (m, 1H).

$^{19}$F-NMR (282.7 MHz, solvent: $CDCl_3$, standard: $CFCl_3$) δ (ppm): −95.2 (ddt, J=36.4, 57.5, 4.7 Hz, 1F), −103.2 (ddd, J=4.7, 15.3, 29.3 Hz, 2F), −106.2 (ddt, J=57.5, 113.9, 29.3 Hz, 1F), −181.32 (ddt, J=36.4, 113.9, 15.3 Hz, 1F).

IR (neat): 2982.2, 2935.9, 1786.3, 1740.6, 1641.7, 1370.9, 1349.8, 1298.8, 1257.7, 1153.1, 1012.9, 912.2, 847.2 cm$^{-1}$.

Example 1-2

Example for Preparation of $CF_2$=$CFCF_2C(C(O)OH)_2CH_2CH$=$CH_2$ (Hereinafter Referred to as Compound $(12^H)$)

The compound $(12^1)$ (6.4 g) was dropwise added to trifluoroacetic acid (60 mL) over a period of 5 minutes with stirring under cooling with ice, and after completion of the dropwise addition, stirring was continued as it was for 2 hours. Then, trifluoroacetic acid was distilled off under reduced pressure at 25° C. to obtain a compound $(12^H)$ (4.6 g).

The NMR data and IR data of the compound $(12^H)$ are shown below.

$^1$H-NMR (300.4 MHz, solvent: $CDCl_3$, standard: TMS) δ (ppm): 2.97 (d, J=7.3 Hz, 2H), 5.20 (dm, J=10.3 Hz, 1H), 5.26 (dm, J=17.1 Hz, 1H), 5.89 (m, 1H), 11.29 (br, 2H).

$^{19}$F-NMR (282.7 MHz, solvent: $CDCl_3$, standard: $CFCl_3$) δ (ppm): −92.4 (ddt, J=37.6, 54.0, 5.8 Hz, 1F), −102.6 (ddd, J=5.8, 15.3, 28.2 Hz, 2F), −105.1 (ddt, J=54.0, 115.0, 28.2 Hz, 1F), −183.0 (ddt, J=37.6, 115.0, 15.3 Hz, 1F).

IR (neat): 3431.5, 3089.4, 2951.5, 1786.8, 1733.6, 1640.8, 1355.6, 1302.5, 1217.0, 1185.5, 1135.3, 1080.9, 934.9, 910.1 cm$^{-1}$.

Example 1-3

Example for Preparation of $CF_2$=$CFCF_2CH(C(O)OH)CH_2CH$=$CH_2$ (Hereinafter Referred to as Compound $(11^H)$)

The compound $(12^H)$ (2.6 g) was mixed with toluene (15 mL), and toluene was distilled off as it was, followed by heating at from 112 to 139° C. for 1 hour. Further, drying under reduced pressure was carried out to obtain a compound $(11^H)$ (1.8 g).

The NMR data and IR data of the compound $(11^H)$ are shown below.

$^1$H-NMR (300.4 MHz, solvent: $CDCl_3$, standard: TMS) δ (ppm): 2.55 (m, 1H), 2.67 (m, 1H), 3.28 (m, 1H), 5.15 (m, 1H), 5.20 (m, 1H) 5.79 (m, 1H), 11.72 (br, 1H).

$^{19}$F-NMR (282.7 MHz, solvent: $CDCl_3$, standard: $CFCl_3$) δ (ppm): −93.6 (ddt, J=36.4, 58.7, 5.4 Hz, 1F), −105.4 (m, 2F), −108.0 (ddt, J=58.7, 115.0, 29.3 Hz, 1F), −186.7 (ddt, J=36.4, 115.0, 15.3 Hz, 1F).

IR (neat) 3088.1, 2931.4, 1788.2, 1726.0, 1646.0, 1423.8, 1366.7, 1309.0, 1257.8, 1171.9, 1067.2, 926.6 cm$^{-1}$.

Example 1-4

Example for Preparation of $CF_2$=$CFCF_2CH(C(O)OC(CH_3)_3)CH_2CH$=$CH_2$ (Hereinafter Referred to as Compound $(11^1)$)

The compound $(11^H)$ is reacted with $(CH_3)_2C$=$CH_2$ under acidic conditions, whereby a compound $(11^1)$ is obtained.

That is, to a reactor, the compound $(11^H)$ (1.77 g) and dichloromethane (10 mL) were added, and three drops of concentrated sulfonic acid (about 0.04 g) were added. The content in the reactor was stirred at 25° C., and $CH_2$=$C(CH_3)_2$ (0.51 g) was added to the reactor with bubbling. The content in the reactor was stirred as it was for 5.5 hours to carry out a reaction, and then a 5% sodium hydrogencarbonate aqueous solution (20 mL) was added to the reactor to quench the reaction. The solution in the reactor was subjected to extraction with tert-butyl methyl ether (50 mL) four times, and the obtained extract was washed with a sodium chloride aqueous solution, dried over sodium sulfate and concentrated. The obtained concentrated product was purified by silica gel column chromatography (developing solvent hexane:ethyl acetate=10:1) to obtain a compound $(11^1)$ (1.31 g).

The NMR data and IR data of the compound $(11^1)$ are shown below.

$^1$H-NMR (300.4 MHz, solvent: $CDCl_3$, standard: TMS) δ (ppm): 1.45 (s, 9H), 2.47 (m, 1H), 2.62 (m, 1H), 3.11 (m, 1H), 5.10 (m, 1H), 5.16 (m, 1H) 5.76 (m, 1H).

$^{19}$F-NMR (282.7 MHz, solvent: $CDCl_3$, standard: $CFCl_3$) δ (ppm): −95.0 (ddt, J=36.4, 62.2, 5.9 Hz, 1F), −104.1 (dm, J=275.8 Hz, 1F), −107.7 (dm, J=275.8 Hz, 1F), −108.9 (ddt, J=62.2, 115.0, 30.5 Hz, 1F), −186.0 (ddt, J=36.4, 115.0, 15.3 Hz, 1F).

IR (neat) 2983.4, 2936.4, 1788.6, 1740.4, 1645.5, 1370.8, 1307.4, 1254.1, 1159.4, 1112.5, 1064.9, 986.8, 926.4, 845.0 cm$^{-1}$.

Example 1-5

Example for Preparation of $CF_2=CFCF_2CH(C(O)OCH_2OCH_3)CH_2CH=CH_2$ (Hereinafter Referred to as Compound ($11^2$))

To a reactor, the compound ($11^H$) (2.30 g) and tert-butyl methyl ether (20 mL) were added, and diisopropylethylamine (1.29 g) was slowly added. Further, $CH_3OCH_2Cl$ (0.79 g) was added, and the content in the reactor was stirred as it was for 2 hours to carry out a reaction. Then, water (30 mL) was added to the reactor to quench the reaction, and an organic layer was separated. The aqueous layer was subjected to extraction with tert-butyl methyl ether (10 mL) twice, and the extract was dried over sodium sulfate and concentrated to obtain a concentrated product, which was purified by silica gel column chromatography (developing solvent hexane:ethyl acetate=5:1) to obtain a compound ($11^2$) (1.97 g).

The NMR data and IR data of the compound ($11^2$) are shown below.

$^1$H-NMR (300.4 MHz, solvent: CDCl$_3$, standard: TMS) δ (ppm): 2.53 (m, 1H), 2.69 (m, 1H), 3.28 (m, 1H), 3.47 (s, 3H), 5.13 (dm, J=10.1 Hz, 1H), 5.19 (dm, J=16.9 Hz, 1H), 5.28 (d, J=5.8 Hz, 1H), 5.31 (d, J=5.8 Hz, 1H), 5.77 (m, 1H).

$^{19}$F-NMR (282.7 MHz, solvent: CDCl$_3$, standard: CFCl$_3$) δ (ppm): −93.8 (dddd, J=4.7, 5.9, 36.4, 59.9 Hz, 1F), −104.9 (dddt, J=5.9, 29.3, 277.0, 15.3 Hz, 1F), −106.0 (dddt, J=4.7, 32.9, 277.0, 12.9 Hz, 1F), −108.2 (dddd, J=29.3, 31.7, 59.9, 115.0 Hz, 1F), −186.6 (dddd, J=14.1, 15.3, 36.4, 115.0 Hz, 1F).

IR (neat) 2964.7, 2836.1, 1788.6, 1752.1, 1645.6, 1351.2, 1308.3, 1243.6, 1169.5, 1096.0, 930.3 cm$^{-1}$.

Example 1-6

Example for Preparation of Compound ($11^3$)

To a solution containing the compound ($11^H$) (2.05 g) and tert-butyl methyl ether (20 mL), diisopropylethylamine (1.15 g) was slowly dropwise added under cooling with ice, and further, the following compound (w$^3$) (1.91 g) was dropwise added. The solution was stirred as it was for 5 hours to carry out a reaction. Then, water was added to the solution to quench the reaction, and an organic layer was recovered. The organic layer was dried over magnesium sulfate and then concentrated to obtain a crude product. The crude product was purified by silica gel column chromatography (developing solvent hexane:ethyl acetate=10:1) to obtain the following compound ($11^3$) (2.1 g).

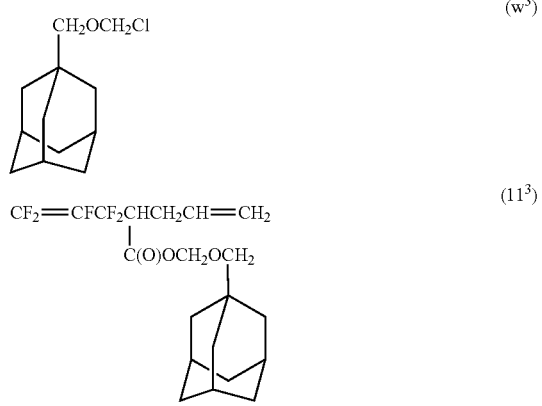

The NMR data and IR data of the compound ($11^3$) are shown below.

$^1$H-NMR (300.4 MHz, solvent: deuterated acetone, standard: TMS) δ (ppm): 1.51-1.97 (15H), 2.48-2.73 (2H), 3.22 (2H), 3.27 (1H) 5.13 (2H), 5.32 (2H), 5.76 (1H).

$^{19}$F-NMR (282.7 MHz, solvent: deuterated acetone, standard: CFCl$_3$) δ (ppm): −94.1 (1F), −105.3 (2F), −108.2 (1F), −186.4 (1F).

IR (neat) 2914.7, 2865.0, 1787.5, 1736.1, 1645.0, 1448.7, 1354.1, 1307.7, 1246.9, 1188.3, 1170.5, 1103.1, 986.7, 925.9, 886.4, 840.1 cm$^{-1}$.

Example 1-7

Example for Preparation of Compound ($11^4$)

To a solution containing the compound ($11^H$) (2.35 g) and toluene (3 mL), two drops of concentrated sulfuric acid were added. Then, under cooling with ice, a toluene solution (3 mL) containing the following compound (w$^4$) (2.04 g) was dropwise added to the solution to carry out a reaction. The solution was stirred as it was for 12 hours, and then a sodium hydrogencarbonate aqueous solution was added to the solution to quench the reaction, and an organic layer was recovered. The organic layer was washed with water and dried over sodium sulfate and then concentrated to obtain a crude product. The crude product was purified by silica gel column chromatography (developing solvent hexane) to obtain the following compound ($11^4$) (2.11 g).

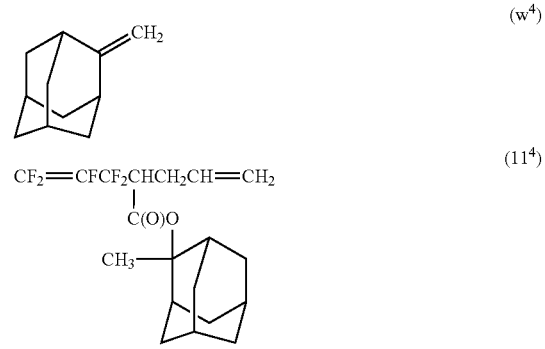

The NMR data and IR data of the compound ($11^4$) are shown below.

$^1$H-NMR (300.4 MHz, solvent: CDCl$_3$, standard: TMS) δ (ppm): 1.57 (m, 2H), 1.59 (s, 3H), 1.69-1.92 (m, 8H), 2.02 (m, 2H), 2.29 (br, 2H), 2.49 (dm, J=14.6 Hz, 1H), 2.66 (dm, J=14.6 Hz, 1H), 3.19 (m, 1H), 5.11 (dm, J=10.1 Hz, 1H), 5.18 (dm, J=17.1 Hz, 1H), 5.79 (ddt, J=10.1, 17.1, 6.9 Hz, 1H).

$^{19}$F-NMR (282.7 MHz, solvent: CDCl$_3$, standard: CFCl$_3$) δ (ppm): −94.6 (dddd, J=4.7, 5.9, 35.2, 61.0 Hz, 1F), −104.4 (dm, J=275.8 Hz, 1F), −106.2 (dm, J=275.8 Hz, 1F), −108.6 (ddt, J=61.0, 115.0, 30.5 Hz, 1F), −185.9 (dddd, J=12.9, 15.3, 36.4, 116.2 Hz, 1F).

IR (neat) 2914.7, 2865.0, 1787.5, 1736.1, 1645.0, 1448.7, 1354.1, 1307.7, 1246.9, 1188.3, 1170.5, 1103.1, 986.7, 925.9, 886.4, 840.1 cm$^{-1}$.

Example 1-8

Example for Preparation of Compound ($11^5$)

To a solution containing the compound ($11^H$) (2.38 g) and dichloromethane (20 mL), a pyridinium salt (0.052 g) of p-toluenesulfonic acid was added. Then, at 25° C., the following compound ($w^5$) (1.60 g) was slowly added to the solution at 25° C., followed by stirring as it was for 3.5 hours. The solution was concentrated, and the obtained crude product was purified by alumina column chromatography (developing solvent hexane:ethyl acetate=10/1) to obtain the following compound ($11^5$) (2.14 g).

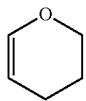
($w^5$)

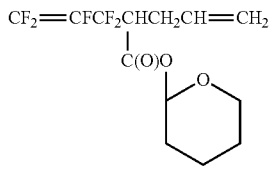
($11^5$)

The NMR data and IR data of the compound ($11^5$) are shown below.

$^1$H-NMR (300.4 MHz, solvent: CDCl$_3$, standard: TMS) δ (ppm): 1.40-1.86 (m, 6H), 2.54 (m, 1H), 2.70 (m, 1H), 3.27 (m, 1H), 3.72 (s, 1H), 3.86 (m, 1H), 5.12 (dm, J=10.3 Hz, 1H), 5.18 (dm, J=17.1 Hz, 1H), 5.79 (ddt, J=6.6, 10.3, 17.1 Hz, 1H), 6.08 (s, 1H).

$^{19}$F-NMR (282.7 MHz, solvent: CDCl$_3$, standard: CFCl$_3$) δ (ppm): −93.7 to −94.2 (m, 1F), −104.1 to −106.8 (m, 2F), −107.8 to −108.7 (m, 1F), −186.0 to −186.9 (m, 1F).

IR (neat) 2951.7, 2877.4, 1788.2, 1749.9, 1644.7, 1357.9, 1307.6, 1246.4, 1173.8, 1133.0, 1056.4, 1037.4, 937.0, 898.4, 860.9 cm$^{-1}$.

Example 1-9

Example for Preparation of Compound ($11^6$)

To a solution containing the compound ($11^H$) (2.0 g) and tert-butyl methyl ether (20 mL), diisopropylethylamine (1.12 g) was slowly dropwise added under cooling with ice, and the following compound ($w^6$) (1.83 g) was dropwise added as it was. The solution was stirred as it was for 5 hours to carry out a reaction. Then, water was added to the solution to quench the reaction, and the organic layer was recovered. The organic layer was dried over magnesium sulfate and concentrated to obtain a crude product. The crude product was purified by silica gel column chromatography (developing solvent hexane:ethyl acetate=10:1) to obtain the following compound ($11^6$) (2.7 g).

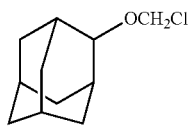
($w^6$)

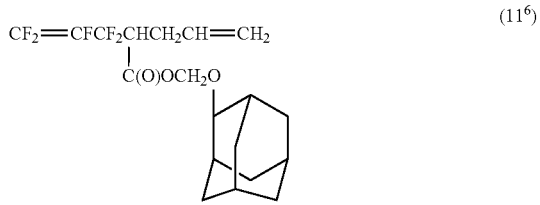
($11^6$)

The NMR data of the compound ($11^6$) are shown below.

$^1$H-NMR (300.4 MHz, solvent: deuterated acetone, standard: TMS) δ (ppm): 1.48-2.05 (15H), 2.47-2.73 (2H), 3.17-3.32 (1H), 5.08-5.21 (2H), 5.43 (2H), 5.69-5.83 (1H).

$^{19}$F-NMR (282.7 MHz, solvent: deuterated acetone, standard: CFCl$_3$) δ (ppm): −94.1 (1F), −105.9 (2F), −108.3 (1F), −186.4 (1F).

Example 1-10

Example for Preparation of Compound ($11^7$)

To a reactor, the compound ($11^H$) (5.0 g), the following compound ($w^7$) (9.9 g), dimethylaminopyridine (0.2 g) and dichloromethane (30 g) were put and cooled to 0° C. Then, a solution having dicyclohexylcarbodiimide (4.7 g) dissolved in dichloromethane (15 g) was slowly dropwise added to the reactor. The solution in the reactor was stirred as it was for 1 hour to carry out a reaction, followed by stirring at 25° C. further for 1 hour to carry out a reaction. The solution in the reactor was subjected to filtration, and the filtrate was concentrated to obtain a crude product. The crude product was purified by silica gel column chromatography (developing solvent hexane:ethyl acetate=20:1) to obtain the following compound ($11^7$) (10.5 g).

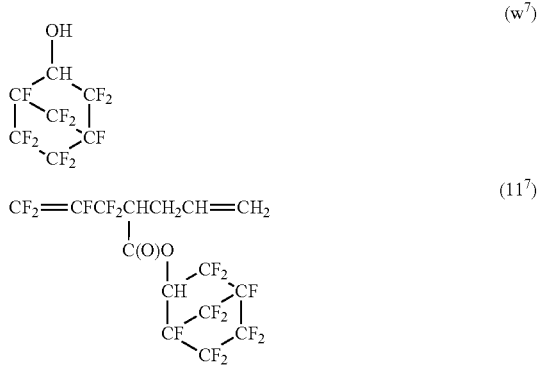

The NMR data of the compound ($11^7$) is shown below.

$^1$H-NMR (300.4 MHz, solvent: deuterated acetone, standard: TMS) δ (ppm): 2.64 to 2.70 (2H), 3.44 to 3.48 (1H), 5.16 to 5.21 (2H), 5.68 to −5.80 (2H).

$^{19}$F-NMR (282.7 MHz, solvent: deuterated acetone, standard: CFCl$_3$) δ (ppm): −92.3 (1F), −105.2 (2F), −107.2 (1F), −123.6 (6F), −132.6 (2F), −187.3 (1F), −214.7 (m, 1F), −223.0 (1F).

The compound ($w^7$) was prepared in accordance with the following preparation scheme (wherein, $R^{f1}$— is F(CF$_2$)$_3$OCF(CF$_3$)CF$_2$OCF(CF$_3$)—).

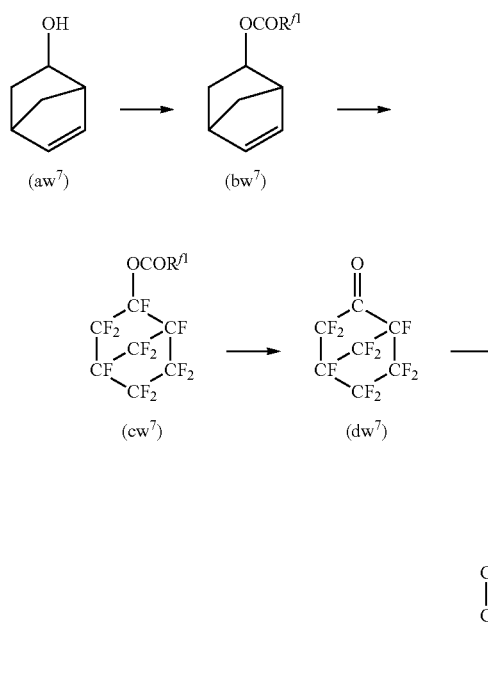

That is, to a flask in a nitrogen gas atmosphere (a compound (aw$^7$) (15 g), chloroform (100 g) and NaF (7.02 g) were put, and R$^{f1}$—COF (79 g) was dropwise added to the flask with stirring under cooling with ice, and the content in the flask was stirred. An insoluble solid material in the flask was removed by pressure filtration, a saturated sodium hydrogencarbonate aqueous solution (103 g) was put in the flask, and the organic layer was recovered and concentrated to obtain a compound (bw$^7$) (74 g).

R113 (313 g) was added to an autoclave provided with a NaF pellet-packed layer at the gas outlet, nitrogen gas was blown to the autoclave for 1 hour while the interior of the autoclave was stirred at 25° C., and then fluorine gas diluted to 20 vol % with nitrogen gas was blown. While the 20% fluorine gas was blown, a solution having a compound (bw$^7$) (67 g) dissolved in R113 (299 g) was injected to the autoclave under a pressure of 0.1 MPa. After completion of the injection, the content in the autoclave was recovered and concentrated to obtain a compound (cw$^7$).

The compound (cw$^7$) (80 g) and powdery KF (0.7 g) were put in a flask in a nitrogen gas atmosphere, the flask was heated for 6 hours, and then the content in the flask was purified to obtain a compound (dw$^7$) (38 g).

NaBH$_4$ (11 g) and THF (30 g) were put in a round-bottom flask in a nitrogen gas atmosphere. While the flask was stirred under cooling with ice, an R225 solution (48 g) containing 22 mass % of the compound (dw$^7$) was dropwise added to the flask. After completion of the dropwise addition, the content in the flask was further stirred, and the solution in the flask was neutralized with a 1N hydrochloric acid aqueous solution (150 mL) to obtain a solution, which was washed with water and purified by distillation to obtain a compound (w$^7$).

The NMR data of the compound (w$^7$) are shown below.

$^1$H-NMR (300.4 MHz, solvent: CDCl$_3$, standard: TMS) δ (ppm): 4.89 to 4.57 (2H).

$^{19}$F-NMR (282.7 MHz, solvent: CDCl$_3$, standard: CFCl$_3$) δ (ppm): −105.0 (1F), −119.7 (1F), −124.0 (1F), −124.3 (1F), −125.7 (1F), −126.8 (1F), −133.2 (2F), −216.6 (1F), −223.5 (1F).

Example 1-11

Example for Preparation of CF$_2$=CFCF$_2$CH(C(O)OCH$_2$CF$_2$CF$_3$)CH$_2$CH=CH$_2$ (Hereinafter Referred to as Compound (11$^8$))

To a reactor, the compound (11$^H$) (5.0 g), CF$_3$CF$_2$CH$_2$OH (3.6 g), dimethylaminopyridine (0.23 g) and dichloromethane (15 mL) were put and cooled to 0° C. Then, a solution having dicyclohexyl carbodiimide (4.9 g) dissolved in dichloromethane (35 mL) was slowly dropwise added to the reactor. The solution in the reactor was stirred as it was for 1 hour to carry out a reaction, and stirring was further carried out at 25° C. for 1 hour to carry out a reaction.

Then, water was added to the reactor to quench the reaction, and an organic layer was recovered. The organic layer was dried over magnesium sulfate and concentrated to obtain a crude product. The crude product was purified by silica gel column chromatography (developing solvent hexane:ethyl acetate=10:1) to obtain a compound (11$^8$) (4.0 g).

The NMR data of the compound (11$^8$) are shown below.

$^1$H-NMR (300.4 MHz, solvent: deuterated acetone, standard: TMS) δ (ppm): 2.51 to 2.73 (2H), 3.30 to 3.44 (1H), 4.50 to 4.69 (2H), 5.07-5.23 (2H), 5.66 to 5.84 (1H).

$^{19}$F-NMR (282.7 MHz, solvent: deuterated acetone, standard: CFCl$_3$) δ (ppm): −84.4 (3F), −94.2 (1F), −105.3 (2F), −107.8 (1F), −124.0 (2F), −187.0 (1F).

Example 1-12

Example for Preparation of Compound (11$^9$)

Three drops of concentrated sulfonic acid were added to a solution containing the compound (11$^H$) (7.6 g) and toluene (30 mL). Then, under cooling with ice, the following compound (w$^9$) (4.1 g) was dropwise added to the solution to carry out a reaction. The temperature was increased to 25° C., and the solution was stirred as it was for 7 hours, and then a sodium hydrogencarbonate aqueous solution was added to the solution to quench the reaction, and an organic layer was recovered. The organic layer was washed with water, dried over sodium sulfate and concentrated to obtain a crude product. The crude product was purified by silica gel column chromatography (developing solvent hexane) to obtain the following compound (11$^9$) (1.78 g).

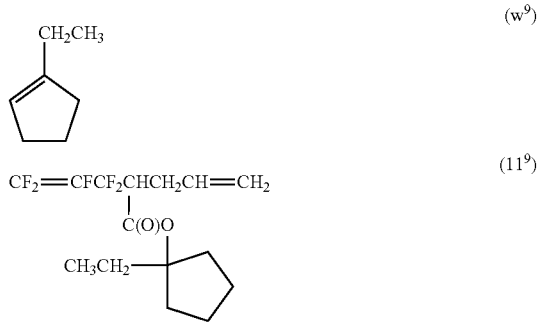

The NMR data and IR data of the compound ($11^9$) are shown below.

$^1$H-NMR (300.4 MHz, solvent: CDCl$_3$, standard: TMS) δ (ppm): 1.57 (m, 2H), 1.59 (s, 3H), 1.69-1.92 (m, 8H), 2.02 (m, 2H), 2.29 (br, 2H), 2.49 (dm, J=14.6 Hz, 1H), 2.66 (dm, J=14.6 Hz, 1H), 3.19 (m, 1H), 5.11 (dm, J=10.1 Hz, 1H), 5.18 (dm, J=17.1 Hz, 1H), 5.79 (ddt, J=10.1, 17.1, 6.9 Hz, 1H).

$^{19}$F-NMR (282.7 MHz, solvent: CDCl$_3$, standard: CFCl$_3$) δ (ppm): −94.6 (dddd, J=4.7, 5.9, 35.2, 61.0 Hz, 1F), −104.4 (dm, J=275.8 Hz, 1F), −106.2 (dm, J=275.8 Hz, 1F), −108.6 (ddt, J=61.0, 115.0, 30.5 Hz, 1F), −185.9 (dddd, J=12.9, 15.3, 36.4, 116.2 Hz, 1F).

IR (neat) 2914.7, 2865.0, 1787.5, 1736.1, 1645.0, 1448.7, 1354.1, 1307.7, 1246.9, 1188.3, 1170.5, 1103.1, 986.7, 925.9, 886.4, 840.1 cm$^{-1}$.

Example 1-13

Example for Preparation of CF$_2$=CFCF$_2$CH(C(O)O(CH$_2$)$_3$C(CF$_3$)$_2$OH)CH$_2$CH=CH$_2$ (Compound ($11^{10}$))

To a reactor, the compound ($11^H$) (CF$_2$=CFCF$_2$CH(C(O)OH)CH$_2$CH=CH$_2$) (1.5 g), HO(CH$_2$)$_3$C(CF$_3$)$_2$OH (1.47 g) dimethylaminopyridine (0.07 g) and dichloromethane (20 g) were put and cooled to 0° C. Then, a 1M dichloromethane solution (9.04 g) of dicyclohexylcarbodiimide was slowly dropwise added to the reactor. The solution in the reactor was stirred at 25° C. for 1 hour to carry out a reaction. The solution in the reactor was subjected to filtration, and the filtrate was concentrated to obtain a crude product. The crude product was purified by silica gel column chromatography (developing solvent hexane:ethyl acetate=15:1) to obtain CF$_2$=CFCF$_2$CH(C(O)O(CH$_2$)$_3$C(CF$_3$)$_2$OH)CH$_2$CH=CH$_2$ (2.4 g) (compound $11^{10}$)).

The NMR data are shown below.

$^1$H-NMR (300.4 MHz, solvent: CDCl$_3$, standard: TMS) δ (ppm): 1.85 to 2.04 (m, 4H), 2.49 to 2.69 (m, 2H), 3.20 to 3.33 (m, 1H), 3.37 (S, 1H), 4.19 to 4.23 (m, 2H), 5.10 to 5.19 (m, 2H), 5.67 to 5.80 (m, 1H).

$^{19}$F-NMR (282.7 MHz, solvent: CDCl$_3$, standard: CFCl$_3$) δ (ppm): −77.0 to −78.1 (m, 6F), −93.5 to −93.9 (m, 1F), −104.6 to −106.7 (m, 2F), −107.8 to −108.6 (m, 1F), −186.3 to −186.9 (m, 1F).

Example 1-14

Example for Preparation of CF$_2$=CFCF$_2$CH(C(O)OCH(CH$_3$)CH$_2$C(CF$_3$)$_2$OH)CH$_2$CH=CH$_2$ (Compound ($11^{11}$))

To a reactor, the compound ($11^H$) (CF$_2$=CFCF$_2$CH(C(O)OH)CH$_2$CH=CH$_2$) (1.0 g), OHCH(CH$_3$)CH$_2$C(CF$_3$)$_2$OH (0.98 g), dimethylaminopyridine (0.07 g) and toluene (20 g) were put and cooled to 0° C. Then, a solution having dicyclohexylcarbodiimide (1.11 g) dissolved in toluene (6 g) was slowly dropwise added to the reactor. The solution in the reactor was stirred at 25° C. for 1 hour, followed by stirring at 40° C. for 3 hours, and stirring was carried out at 70° C. further for 2 hours to carry out a reaction. The solution in the reactor was subjected to filtration, and the filtrate was concentrated to obtain a crude product. The crude product was purified by silica gel column chromatography (developing solvent hexane:ethyl acetate=25:1) to obtain CF$_2$=CFCF$_2$CH(C(O)OCH(CH$_3$)CH$_2$C(CF$_3$)$_2$OH)CH$_2$CH=CH$_2$ (1.14 g) (compound ($11^{11}$)).

The NMR data are shown below.

$^1$H-NMR (300.4 MHz, solvent: CDCl$_3$, standard: TMS) δ (ppm): 1.26 to 1.43 (m, 3H), 2.21 to 2.26 (m, 2H), 2.50 to 2.70 (m, 2H), 3.19 to 3.31 (m, 1H), 4.84 to 4.87 (m, 1H), 5.13 to 5.25 (m, 3H), 5.67 to 5.77 (m, 1H).

$^{19}$F-NMR (282.7 MHz, solvent: CDCl$_3$, standard: CFCl$_3$) δ (ppm): −76.5 to −79.6 (md, J=627.8, 6F), −92.9 to −93.3 (m, 1F), −103.2 to −108.1 (m, 3F), −186.4 to −187.1 (m, 1F).

Example 1-15

Example for Preparation of CF$_2$=CFCF$_2$CH(C(O)OCH(CH$_2$C(CF$_3$)$_2$OH)$_2$)CH$_2$CH=CH$_2$ (Compound ($11^{12}$))

To a reactor, the compound ($11^H$) (CF$_2$=CFCF$_2$CH(C(O)OH)CH$_2$CH=CH$_2$) (1.0 g), OHCH(CH$_2$C(CF$_3$)$_2$OH)$_2$ (1.7 g), dimethylaminopyridine (0.14 g), dichloromethane (10 g) and toluene (30 g) were put and cooled to 0° C. Then, a 1M dichloromethane solution (6.03 g) of dicyclohexylcarbodiimide was slowly dropwise added to the reactor. The solution in the reactor was stirred at 25° C. for 2 hours to carry out a reaction. The solution in the reactor was subjected to filtration, and the filtrate was concentrate to obtain a crude product. The crude product was purified by silica gel column chromatography (developing solvent hexane:ethyl acetate=20:1) to obtain CF$_2$=CFCF$_2$CH(C(O)OCH(CH$_2$C(CF$_3$)$_2$OH)$_2$)CH$_2$CH=CH$_2$ (1.13 g) (compound ($11^{12}$)).

The NMR data are shown below.

$^1$H-NMR (300.4 MHz, solvent: CDCl$_3$, standard: TMS) δ (ppm): 2.31 to 2.41 (m, 2H), 2.59 to 2.73 (m, 4H), 3.37 to 3.51 (m, 1H), 5.06 to 5.22 (m, 2H), 5.70 to 5.90 (m, 2H), 7.09 (s, 2H).

$^{19}$F-NMR (282.7 MHz, solvent: CDCl$_3$, standard: CFCl$_3$) δ (ppm): −75.5 to −78.6 (m d, J=239.8, 12F), −93.9 to −95.1 (m, 1F), −103.2 to −105.5 (m, 2F), −107.5 to −108.4 (m, 1F), −185.8 to −186.5 (m, 1F).

Example 2

Example for Preparation of Polymer

Example 2-1

Example for Preparation of Polymer (1)

To a pressure resistant reactor (internal capacity: 30 mL, made of glass), the compound ($12^1$) (1.51 g) and ethyl acetate (3.41 g) were charged. Then, an R225 solution (0.20 g) containing 50 mass % of IPP as a polymerization initiator was added to the pressure resistant reactor. The reactor was freeze-deaerated, and polymerization was carried out for 18 hours while the reactor was kept at 40° C. The solution in the reactor was dropwise added to methanol, and the formed solid material was recovered and vacuum-dried at 80° C. for 20 hours to obtain a polymer (1) (0.84 g) as a white powder at 25° C.

Of the polymer (1), Mw was 6,300 and Mn was 4,600.

Further, as a result of analyzing the polymer (1) by $^{19}$F-NMR and $^1$H-NMR, the polymer (1) was confirmed to contain at least one type of repeating units (U$12^1$) selected from the group consisting of repeating units represented by the following formulae (U1-$12^1$), (U2-$12^1$) and (U3-$12^1$).

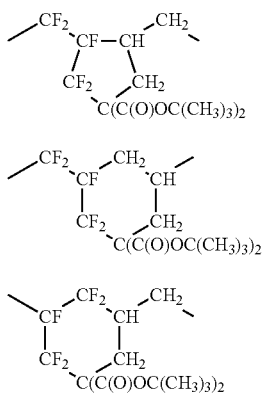

(U1-12$^1$)

(U2-12$^1$)

(U3-12$^1$)

The polymer (1) was soluble in acetone, THF, ethyl acetate, methanol and 2-perfluorohexyl ethanol, and insoluble in R225, perfluoro(2-butyltetrahydrofuran) and perfluoro-n-octane.

Example 2-2

Example for Preparation of Polymer (2)

To a pressure resistant reactor (internal capacity: 20 mL, made of glass), the compound (12$^H$) (1.00 g), R225 (5.41 g) and IPP (0.10 g) were charged. Then, an R225 solution (0.28 g) containing 50 mass % of IPP was added to the pressure resistant reactor as a polymerization initiator. The reactor was freeze-deaerated, and polymerization was carried out for 18 hours while the reactor was kept at 40° C. The solvent in the reactor was changed to THF, and the solution was dropwise added to hexane, and the formed solid material was recovered and vacuum-dried at 80° C. for 20 hours to obtain a polymer (2) (0.82 g) as a white powder at 25° C.

Of the polymer (2), Mw was 22,100 and Mn was 8,700.

Further, as a result of analyzing the polymer (2) by $^{19}$F-NMR and $^1$H-NMR, the polymer (2) was confirmed to contain at least one type of repeating units (U12$^H$) selected from the group consisting of repeating units represented by the following formulae (U1-12$^H$), (U2-12$^H$) and (U3-12$^H$).

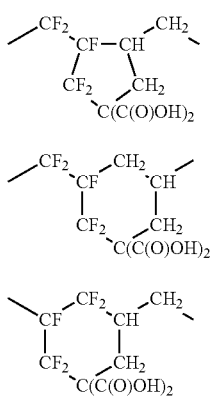

(U1-12$^H$)

(U2-12$^H$)

(U3-12$^H$)

When the polymer (2), sodium hydroxide and CH$_3$OCH$_2$Cl are reacted in methanol, a polymer containing any one type of repeating units represented by the following formulae is obtained.

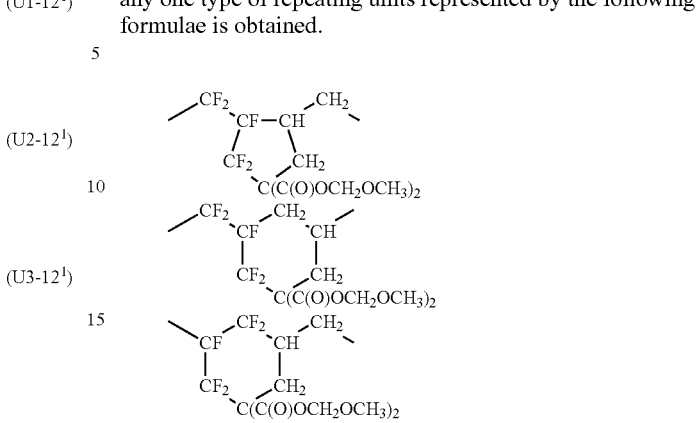

Example 2-3

Example for Preparation of Polymer (3)

To a reactor (internal capacity: 200 mL, made of glass), the compound (11$^H$) (16.0 g) and ethyl acetate (129.8 g) were charged, and as a polymerization initiator, IPP (5.95 g) as a 50 mass % R225 solution was added. The reactor was deaerated under reduced pressure, and polymerization reaction was carried out at an internal temperature of the reactor of 40° C. for 18 hours. The solution in the reactor was dropwise added to hexane, and the obtained solid material was recovered and vacuum-dried at 120° C. for 40 hours to obtain a polymer (3) (15.5 g) as a white powder at 25° C.

Of the polymer (3), Mw was 9,700 and Mn was 4,600, and Tg was 178° C. Further, as a result of analyzing the polymer (3) by $^{19}$F-NMR and $^1$H-NMR, the polymer (3) was confirmed to contain at least one type of repeating units (U11$^H$) selected from the group consisting of repeating units represented by the following formulae (U1-11$^H$), (U2-11$^H$) and (U3-11$^H$).

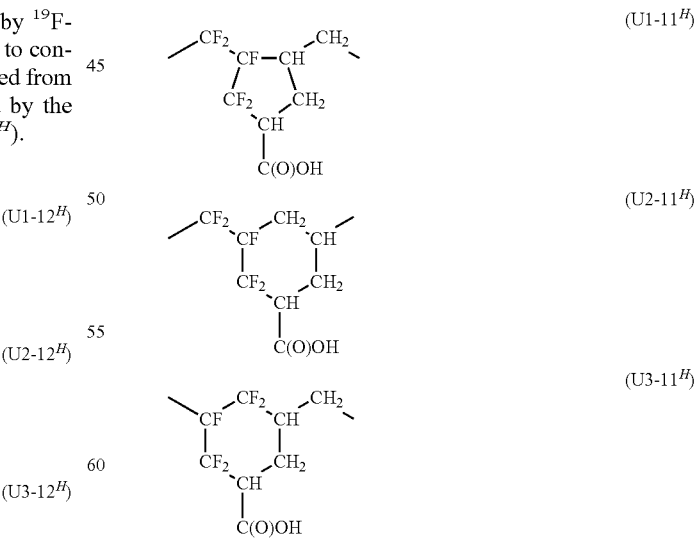

(U1-11$^H$)

(U2-11$^H$)

(U3-11$^H$)

The polymer (3) was soluble in acetone, THF, ethyl acetate, methanol and PGMEA, and insoluble in R225, perfluoro(2-butyltetrahydrofuran) and perfluoro-n-octane.

Example 2-4

Example for Preparation of Polymer (4)

To a reactor (internal capacity: 30 mL, made of glass), the compound (11[1]) (0.8 g), R225 (8.0 g) and IPA (0.06 g) were charged, and as a polymerization initiator, IPP (1.0 g) as a 50 mass % R225 solution was added. The reactor was deaerated under reduced pressure, and polymerization reaction was carried out at an internal temperature of the reactor of 40° C. for 18 hours. The solution in the reactor was dropwise added to hexane (90 g), and the obtained solid material was recovered and vacuum-dried at 90° C. for 40 hours to obtain a polymer (4) (0.56 g) as a white powder at 25° C.

Of the polymer (4), Mw was 16,000 and Mn was 11,000, and Tg was 118° C. Further, as a result of analyzing the polymer (4) by $^{19}$F-NMR and $^{1}$H-NMR, the polymer (4) was confirmed to contain at least one type of repeating units (U11[1]) selected from the group consisting of repeating units represented by the following formulae (U1-11[1]), (U2-11[1]) and (U3-11[1]).

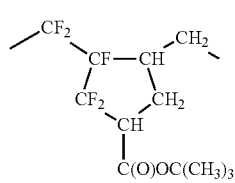
(U1-11[1])

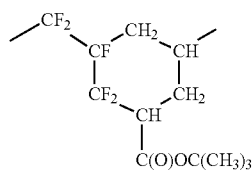
(U2-11[1])

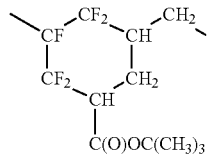
(U3-11[1])

The polymer (4) was soluble in acetone, THF, ethyl acetate and PGMEA, and insoluble in R225, perfluoro(2-butyltetrahydrofuran) and perfluoro-n-octane.

Example 2-5

Example for Preparation of Polymer (5)

To a reactor (internal capacity: 30 mL, made of glass), the compound (11[2]) (0.8 g), R225 (4.3 g) and IPA (0.07 g) were charged, and as a polymerization initiator, IPP (0.53 g) as a 50 mass % R225 solution was added. The reactor was deaerated under reduced pressure, and polymerization reaction was carried out at an internal temperature of the reactor of 40° C. for 18 hours. The solution in the reactor was dropwise added to hexane (60 g), and the obtained solid material was recovered and vacuum-dried at 90° C. for 40 hours to obtain a polymer (5) (0.6 g) as a white powder at 25° C.

Of the polymer (5), Mw was 15,800 and Mn was 8,900.

By NMR analysis, the polymer (5) was confirmed to contain at least one type of repeating units (U11[2]) selected from the group consisting of repeating units represented by the following formulae (U1-11[2]), (U2-11[2]) and (U3-11[2]).

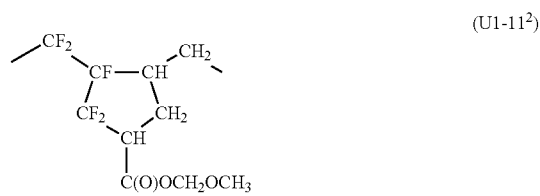
(U1-11[2])

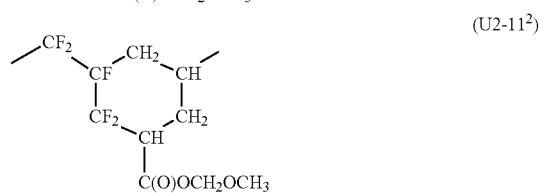
(U2-11[2])

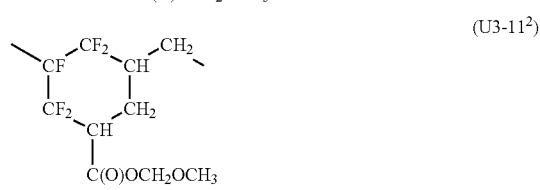
(U3-11[2])

The polymer (5) was soluble in acetone, THF, ethyl acetate and PGMEA, and insoluble in R225, perfluoro(2-butyltetrahydrofuran) and perfluoro-n-octane.

Example 2-6

Example for Preparation of Polymer (6)

To a reactor (internal capacity: 30 mL, made of glass), the compound (11[3]) (2.0 g) and ethyl acetate (15.8 g) were charged, IPP (0.73 g) as a 50 mass % R225 solution was charged, and a polymerization reaction was carried out at 40° C. for 18 hours. The solution in the reactor was dropwise added to hexane, and the obtained solid material was recovered and vacuum-dried at 90° C. for 24 hours to obtain a polymer (6) (1.40 g).

Of the polymer (6), Mw was 12,600 and Mn was 6,100, and Tg was 90° C. By NMR analysis, the polymer (6) was confirmed to contain at least one type of repeating units (U11[3]) selected from the group consisting of repeating units represented by the following formulae (U1-11[3]), (U2-11[3]) and (U3-11[3]).

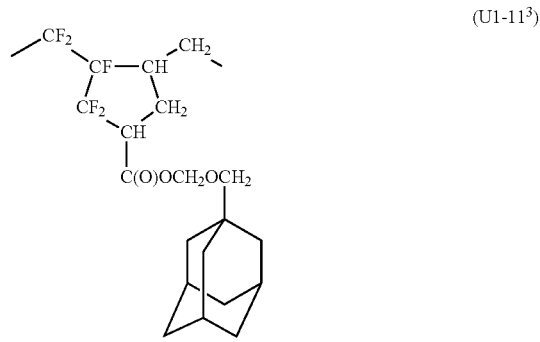
(U1-11[3])

-continued

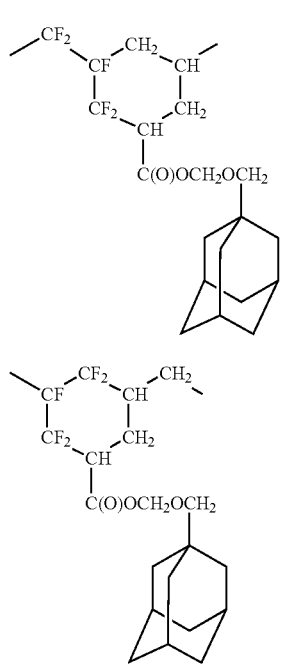

(U2-11³)

(U3-11³)

(U2-11⁴)

(U3-11⁴)

The polymer (6) was in the form of a white powder at 25° C., and soluble in acetone, tetrahydrofuran and ethyl acetate.

Example 2-7

Example for Preparation of Polymer (7)

To a reactor (internal capacity: 30 mL), the compound (11⁴) (2.0 g) and ethyl acetate (11.0 g) were charged, IPP (0.53 g) as a 50 mass % R225 solution was charged, and a polymerization reaction was carried out at 40° C. for 18 hours. The solution in the reactor was dropwise added to hexane, and the obtained solid material was recovered and vacuum-dried at 110° C. for 24 hours to obtain a polymer (7) (1.90 g).

Of the polymer (7), Mw was 23,500 and Mn was 9,600, and Tg was 161° C.

By NMR analysis, the polymer (7) was confirmed to contain at least one type of repeating units (U11⁴) selected from the group consisting of repeating units represented by the following formulae (U1-11⁴), (U2-11⁴) and (U3-11⁴).

The polymer (7) was in the form of a white powder at 25° C., and soluble in tetrahydrofuran and ethyl acetate.

Example 2-8

Example for Preparation of Polymer (8)

To a reactor (internal capacity: 30 mL), the compound (11⁶) (1.0 g) and ethyl acetate (8.8 g) were charged, IPP (0.40 g) as a 50 mass % R225 solution was charged, and a polymerization reaction was carried out at 40° C. for 18 hours. The solution in the reactor was dropwise added to methanol, and the obtained solid material was recovered and vacuum-dried at 90° C. for 24 hours to obtain a polymer (8) (0.62 g).

Of the polymer (8), Mn was 6,100 and Mw was 10,200, and Tg was 107° C. By NMR analysis, the polymer (8) was confirmed to contain at least one type of repeating units (U11⁶) selected from the group consisting of repeating units represented by the following formulae (U1-11⁶), (U2-11⁶) and (U3-11⁶).

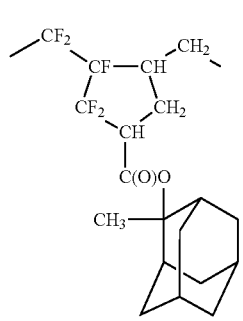

(U1-11⁴)

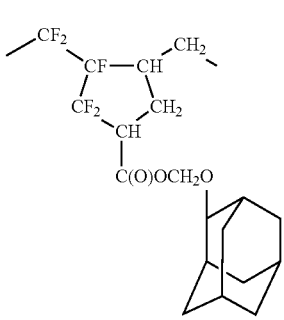

(U1-11⁶)

-continued (U2-11⁶)

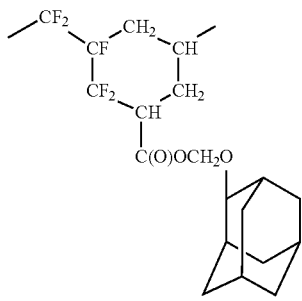

(U3-11⁶)

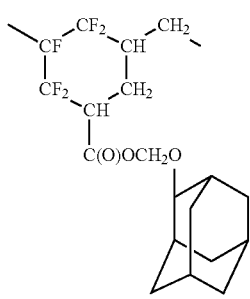

Example 2-9

Example for Preparation of Polymer (9)

To a reactor (internal capacity: 30 mL), the compound (11⁷) (0.5 g) and R225 (1.93 g) were charged, IPP (0.15 g) as a 50 mass % R225 solution was charged, and a polymerization reaction was carried out at 40° C. for 18 hours. The solution in the reactor was dropwise added to hexane, and the obtained solid material was recovered and vacuum-dried at 100° C. for 24 hours to obtain a polymer (9) (0.42 g).

Of the polymer (9), Mn was 9,900 and Mw was 15,100.

By NMR analysis, the polymer (9) was confirmed to contain at least one type of repeating units (U11⁷) selected from the group consisting of repeating units represented by the following formulae (U1-11⁷), (U2-11⁷) and (U3-11⁷).

(U1-11⁷)

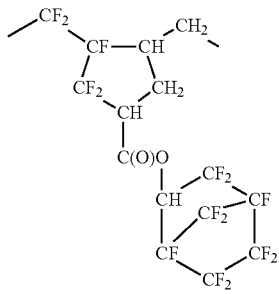

-continued (U2-11⁷)

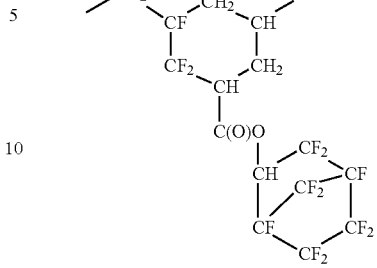

(U3-11⁷)

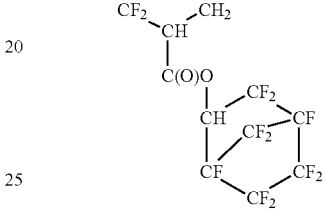

The polymer (9) was in the form of a white powder at 25° C., and soluble in acetone, THF, methanol and R225.

Example 2-10

Example for Preparation of Polymer (10)

To a reactor (internal capacity: 30 mL), the compound (11⁸) (0.81 g) and R225 (7.2 g) were charged, IPP (0.81 g) as a 50 mass % R225 solution was charged, and a polymerization reaction was carried out at 40° C. for 18 hours. The solution in the reactor was dropwise added to hexane, and the obtained solid material was recovered and vacuum-dried at 90° C. for 24 hours to obtain a polymer (10) (0.66 g).

Of the polymer (10), Mn was 4,300 and Mw was 6,600.

By NMR analysis, the polymer (10) was confirmed to contain at least one type of repeating units (U11⁸) selected from the group consisting of repeating units represented by the following formulae (U1-11⁸), (U2-11⁸) and (U3-11⁸).

(U1-11⁸)

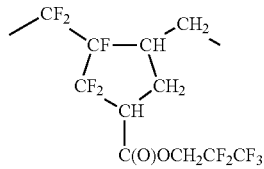

(U2-11⁸)

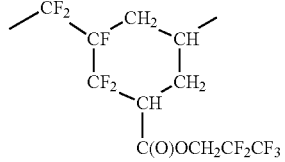

-continued

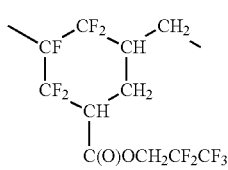
(U3-11⁸)

Example 2-11

Example for Preparation of Polymer (11)

To a reactor (internal capacity: 30 mL), the compound (11⁹) (0.89 g) and ethyl acetate (7.8 g) were charged, IPP (0.35 g) as a 50 mass % R225 solution was charged, and a polymerization reaction was carried out at 40° C. for 18 hours. The solution in the reactor was dropwise added to hexane, and the obtained solid material was recovered and vacuum-dried at 90° C. for 24 hours to obtain a polymer (11) (0.80 g).

Of the polymer (11), Mn was 7,500 and Mw was 16,000.

By NMR analysis, the polymer (11) was confirmed to contain at least one type of repeating units (U11⁹) selected from the group consisting of repeating units represented by the following formulae (U1-11⁹), (U2-11⁹) and (U3-11⁹).

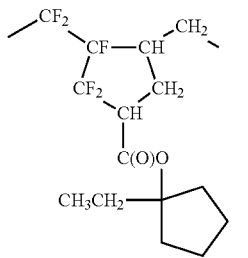
(U1-11⁹)

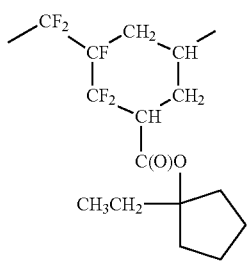
(U2-11⁹)

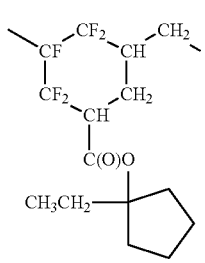
(U3-11⁹)

The polymer (11) was in the form of a white powder at 25° C., and soluble in tetrahydrofuran and ethyl acetate.

Example 2-12

Example for Preparation of Polymer (12)

To a reactor (internal capacity: 30 mL, made of glass), the compound (11$^H$) (0.67 g), the compound (11²) (2.8 g) and ethyl acetate (22.7 g) were charged, and as a polymerization initiator, IPP (1.1 g) as a 50 mass % R225 solution was added. The reactor was deaerated under reduced pressure, and a polymerization reaction was carried out at an internal temperature of the reactor of 40° C. for 18 hours. The solution in the reactor was dropwise added to hexane (270 g), and the obtained solid material was recovered and vacuum-dried at 110° C. for 40 hours to obtain a polymer (12) (2.55 g) as a white powder at 25° C.

Of the polymer (12), Mw was 15,400, and Mn was 8,300.

By NMR analysis, the polymer (12) was confirmed to be a polymer containing repeating units (U11$^H$) and repeating units (U11²) and to contain 36 mol % of the repeating units (U11$^H$) and 64 mol % of the repeating units (U11²) based on all the repeating units.

The polymer (12) was soluble in acetone, THF, ethyl acetate, methanol and PGMEA, and insoluble in R225, perfluoro(2-butyltetrahydrofuran) and perfluoro-n-octane.

Example 2-13

Example for Preparation of Polymer (13)

To a reactor (internal capacity: 30 mL, made of glass), the compound (11$^H$) (0.07 g), the compound (11¹) (0.75 g) and ethyl acetate (1.85 g) were charged, and as a polymerization initiator, IPP (0.11 g) as a 50 mass % R225 solution was added. The reactor was deaerated under reduced pressure, and a polymerization reaction was carried out at an internal temperature of the reactor of 40° C. for 18 hours. The solution in the reactor was dropwise added to hexane, and the obtained solid material was recovered and vacuum-dried at 90° C. for 24 hours to obtain a polymer (13) (0.67 g).

Of the polymer (13), Mw was 28,000, and Mn was 14,500.

By NMR analysis, the polymer (13) was confirmed to be a polymer containing repeating units (U11$^H$) and repeating units (U11¹) and to contain 12 mol % of the repeating units (U11$^H$) and 88 mol % of the repeating units (U11¹) based on all the repeating units.

Example 2-14

Example for Preparation of Polymer (14)

To a reactor (internal capacity: 30 mL, made of glass), the compound (11⁴) (0.75 g), the compound (11⁸) (0.18 g) and ethyl acetate (6.7 g) were charged, and as a polymerization initiator, IPP (0.31 g) as a 50 mass % R225 solution was added. The reactor was deaerated under reduced pressure, and a polymerization reaction was carried out at an internal temperature of the reactor of 40° C. for 18 hours. The solution in the reactor was dropwise added to hexane, and the obtained solid material was recovered and vacuum-dried at 90° C. for 24 hours to obtain a polymer (14) (0.61 g).

Of the polymer (14), Mw was 18,900, and Mn was 10,600.

By NMR analysis, the polymer (14) was confirmed to be a polymer containing repeating units (U11⁴) and repeating units (U11⁸) and to contain 77 mol % of the repeating units (U11⁴) and 23 mol % of the repeating units (U11⁸) based on all the repeating units.

Example 2-15

Example for Preparation of Polymer (15)

To a reactor (internal capacity: 30 mL, made of glass), the compound ($11^H$) (0.20 g), the compound ($11^7$) (0.45 g) and ethyl acetate (5.7 g) were charged, and as a polymerization initiator, IPP (0.26 g) as a 50 mass % R225 solution was added. The reactor was deaerated under reduced pressure, and a polymerization reaction was carried out at an internal temperature of the reactor of 40° C. for 18 hours. The solution in the reactor was dropwise added to hexane, and the obtained solid material was recovered and vacuum-dried at 100° C. for 24 hours to obtain a polymer (15) (0.51 g).

Of the polymer (15), Mw was 15,400, and Mn was 8,300.

As a result of analyzing the polymer (15) by NMR, the polymer (15) was confirmed to be a polymer containing repeating units ($U11^H$) and repeating units ($U11^7$) and to contain 52 mol % of the repeating units ($U11^H$) and 48 mol % of the repeating units ($U11^7$) based on all the repeating units. Further, the polymer (15) was soluble in acetone, THF, ethyl acetate and methanol.

Example 2-16

Example for Preparation of Polymer (16)

To a pressure resistant reactor (internal capacity: 30 mL, made of glass), a compound ($CF_2$=$CFCF_2CH(C(O)O(CH_2)_3C(CF_3)_2OH)CH_2CH$=$CH_2$) (compound ($11^{10}$)) (1.0 g) and ethyl acetate (7.0 g) were charged. Then, an R225 solution (0.67 g) containing 50 mass % of IPP was added as a polymerization initiator to the pressure resistant reactor. The reactor was freeze-deaerated, and polymerization was carried out for 18 hours while the reactor was kept at 40° C. The solution in the reactor was dropwise added to hexane, and the formed solid material was recovered and vacuum-dried at 80° C. for 18 hours to obtain a polymer (16) (1.64 g) as a white powder at 25° C.

Of the polymer (16), Mw was 9,700, and Mn was 5,800.

Further, as a result of analyzing the polymer (16) by $^{19}$F-NMR and $^1$H-NMR, the polymer (16) was confirmed to contain at least one type of repeating units ($U11^{10}$) selected from the group consisting of repeating units represented by the following formulae ($U1-11^{10}$), ($U2-11^{10}$) and ($U3-11^{10}$).

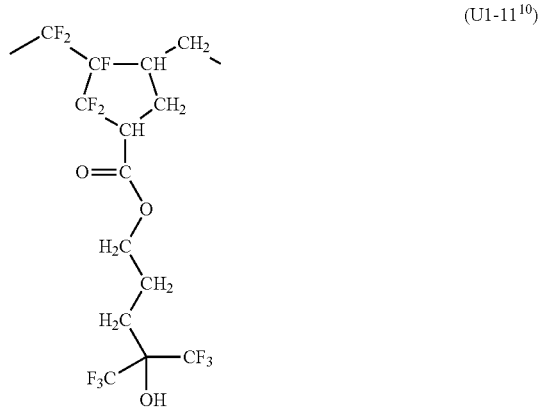

(U1-11$^{10}$)

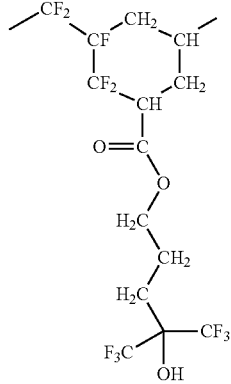

(U2-11$^{10}$)

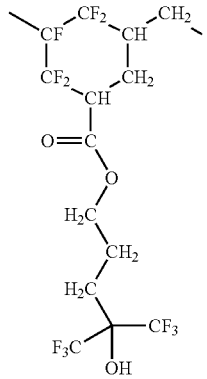

(U3-11$^{10}$)

The polymer (16) was soluble in acetone, THF, ethyl acetate and methanol.

Example 2-17

Example for Preparation of Polymer (17)

To a pressure resistant reactor (internal capacity: 30 mL, made of glass), a compound ($CF_2$=$CFCF_2CH(C(O)OCH(CH_3)CH_2C(CF_3)_2OH)CH_2CH$=$CH_2$) (compound ($11^{11}$)) (0.8 g) and ethyl acetate (3.6 g) were charged. Then, an R225 solution (0.363 g) containing 50 mass % of IPP was added as a polymerization initiator to the pressure resistant reactor. The reactor was freeze-deaerated, and polymerization was carried out for 18 hours while the reactor was kept at 40° C. The solution in the reactor was dropwise added to hexane, and the formed solid material was recovered and vacuum-dried at 80° C. for 24 hours to obtain a polymer (17) (0.4 g) as a white powder at 25° C.

Of the polymer (17), Mw was 9,000, and Mn was 6,000.

Further, as a result of analyzing the polymer (17) by $^{19}$F-NMR and $^1$H-NMR, the polymer (16) was confirmed to contain at least one type of repeating units ($U11^{11}$) selected from the group consisting of repeating units represented by the following formulae ($U1-11^{11}$), ($U2-11^{11}$) and ($U3-11^{11}$).

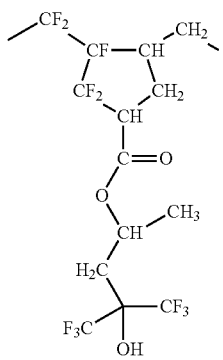
(U1-11¹¹)

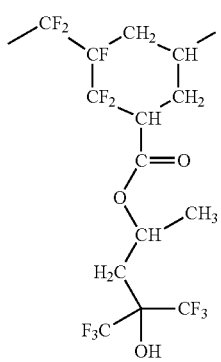
(U2-11¹¹)

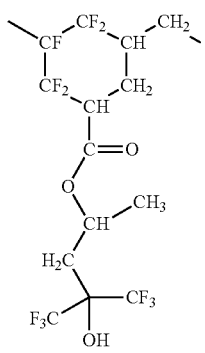
(U3-11¹¹)

The polymer (17) was soluble in acetone, THF, ethyl acetate and methanol.

Example 2-18

Example for Preparation of Polymer (18)

To a reactor (internal capacity: 30 mL, made of glass), the compound (11$^H$) ($CF_2$=$CFCF_2CH(C(O)OH)CH_2CH$=$CH_2$) (0.10 g), a compound ($CF_2$=$CFCF_2CH(C(O)O(CH_2)_3C(CF_3)_2OH)CH_2CH$=$CH_2$) (0.52 g) and ethyl acetate (4.9 g) were charged, and IPP (0.22 g) as a 50 mass % R225 solution was added as a polymerization initiator. The reactor was deaerated under reduced pressure, and a polymerization reaction was carried out at an internal temperature of the reactor of 40° C. for 18 hours. The solution in the reactor was dropwise added to hexane, and the obtained solid material was recovered and vacuum-dried at 90° C. for 24 hours to obtain a polymer (18) (0.45 g).

Of the polymer (18), Mw was 11,900, and Mn was 6,400.

As a result of analyzing the polymer (18) by NMR, the polymer (18) was confirmed to be a polymer containing the repeating units (U11H) and repeating units ($CF_2$=$CFCF_2CH(C(O)O(CH_2)_3C(CF_3)_2OH)CH_2CH$=$CH_2$), and to be a polymer containing 23 mol % of the repeating units (U11$^H$) and 77 mol % of the repeating units ($CF_2$=$CFCF_2CH(C(O)O(CH_2)_3C(CF_3)_2OH)CH_2CH$=$CH_2$) based on all the repeating units. Further, the polymer (18) was soluble in acetone, THF, ethyl acetate and methanol.

Example 2-19

Example for Preparation of Polymer (19)

To a reactor (internal capacity: 30 mL, made of glass), the compound (11$^H$) ($CF_2$=$CFCF_2CH(C(O)OH)CH_2CH$=$CH_2$) (0.10 g), a compound ($CF_2$=$CFCF_2CH(C(O)OCH(CH_3)CH_2C(CF_3)_2OH)CH_2CH$=$CH_2$) (0.44 g) and ethyl acetate (4.8 g) were charged, and IPP (0.22 g) as a 50 mass % R225 solution was added as a polymerization initiator. The reactor was deaerated under reduced pressure, and a polymerization reaction was carried out at an internal temperature of the reactor of 40° C. for 18 hours. The solution in the reactor was dropwise added to hexane, and the obtained solid material was recovered and vacuum-dried at 90° C. for 24 hours to obtain a polymer (19) (0.39 g).

Of the polymer (19), Mw was 11,600, and Mn was 6,500.

As a result of analyzing the polymer (19) by NMR, the polymer (19) was confirmed to be a polymer containing the repeating units (U11$^H$) and repeating units ($CF_2$=$CFCF_2CH(C(O)OCH(CH_3)CH_2C(CF_3)_2OH)CH_2CH$=$CH_2$), and to be a polymer containing 28 mol % of the repeating units (U11$^H$) and 72 mol % of the repeating units ($CF_2$=$CFCF_2CH(C(O)OCH(CH_3)CH_2C(CF_3)_2OH)CH_2CH$=$CH_2$) based on all the repeating units. Further, the polymer (19) was soluble in acetone, THF, ethyl acetate and methanol.

Example 2-20

Example for Preparation of Polymer (20)

To a pressure resistant reactor (internal capacity: 30 mL, made of glass), a compound ($CF_2$=$CFCF_2CH(C(O)OCH(CH_2C(CF_3)_2OH)_2)CH_2CH$=$CH_2$) (compound (11$^{12}$)) (0.5 g) and ethyl acetate (4.4 g) were charged. Then, an R225 solution (0.2 g) containing 50 mass % of IPP was added as a polymerization initiator to the pressure resistant reactor. The reactor was freeze-deaerated, and polymerization was carried out for 18 hours while the reactor was kept at 40° C. The solution in the reactor was dropwise added to hexane, and the formed solid material was recovered and vacuum-dried at 90° C. for 24 hours to obtain a polymer (20) (0.28 g) as a white powder at 25° C.

Of the polymer (20), Mw was 10,300, and Mn was 6,800.

Further, as a result of analyzing the polymer (20) by $^{19}$F-NMR and $^1$H-NMR, the polymer (20) was confirmed to contain at least one type of repeating units (U11$^{12}$) selected from the group consisting of repeating units represented by the following formulae (U1-11$^{12}$), (U2-11$^{12}$) and (U3-11$^{12}$).

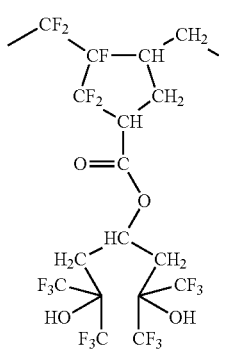

(U1-11¹⁰)

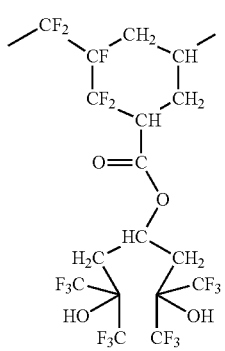

(U2-11¹⁰)

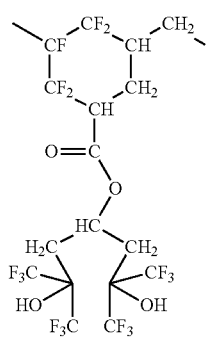

(U3-11¹⁰)

The polymer (20) was soluble in acetone, THF, ethyl acetate and methanol.

Example 3

Evaluation Example of Water Repellency of Polymer

The polymer (1) was dissolved in PGMEA to prepare a PGMEA solution containing 10 mass % of the polymer (1), and the solution was filtrated through a filter (made of polytetrafluoroethylene, pore size: 0.2 μm) to obtain a resin solution.

Then, a silicon substrate having an antireflection film (manufactured by ROHM AND HAAS Electronic Materials, tradename: AR26) on its surface, was spin-coated with the resin solution, and the silicon substrate was heat-treated at 100° C. for 90 seconds to obtain a resin thin film comprising the polymer (1) on the silicon substrate. Then, the static contact angle, the sliding angle, the advancing angle and the receding angle of the resin thin film to water were measured. For the measurement, a contact angle meter DM-700 manufactured by Kyowa Interface Science Co., Ltd. was used. Further, the volume of water drops used was 2 μL in the case of the contact angle, and 50 μL in the case of the sliding angle, the advancing angle and the receding angle. Further, the sliding angle measured by means of a sliding method will be referred to as "sliding angle", the advancing contact angle will be referred to as "advancing angle", and the receding contact angle will be referred to as "receding angle". The units of the static contact angle, the sliding angle, the advancing angle and the receding angle were degree (°).

Further, the static contact angle, the sliding angle, the advancing angle and the receding angle were measured in the same manner except that the polymer (4) or (5) was used instead of the polymer (1). The results are summarized in Table 1.

TABLE 1

| Material for forming a resin thin film | Static contact angle | Sliding angle | Advancing angle | Receding angle |
|---|---|---|---|---|
| Polymer (1) | 86 | 9 | 89 | 79 |
| Polymer (4) | 88 | 8 | 91 | 83 |
| Polymer (5) | 75 | 21 | 81 | 61 |

Further, resin thin films were formed in the same method except that a solution containing each of the polymers (2), (3), (6) to (11), (13), (14) and (15) was used instead of the PGMEA solution containing 10 mass % of the polymer (1), and the static contact angle, the sliding angle, the advancing angle and the receding angle were measured. Further, with respect to the polymers (16) to (20), a solution containing a 4-methyl-2-pentanol solution containing 4 mass % of each of the polymers (16) to (20) was used. The results are summarized in Table 2.

TABLE 2

| Material for forming a resin thin film | Static contact angle | Sliding angle | Advancing angle | Receding angle |
|---|---|---|---|---|
| Polymer (2) | 54 | 48 | 70 | 23 |
| Polymer (3) | 56 | 44 | 67 | 21 |
| Polymer (6) | 86 | 14 | 89 | 75 |
| Polymer (7) | 87 | 8 | 87 | 80 |
| Polymer (8) | 82 | 14 | 86 | 73 |
| Polymer (9) | 103 | 12 | 105 | 92 |
| Polymer (10) | 98 | 15 | 86 | 73 |
| Polymer (11) | 86 | 9 | 90 | 80 |
| Polymer (13) | 86 | 14 | 89 | 75 |
| Polymer (14) | 89 | 12 | 92 | 80 |
| Polymer (15) | 96 | 50 | 101 | 53 |
| Polymer (16) | 74 | 19 | 82 | 63 |
| Polymer (17) | 80 | 15 | 84 | 69 |
| Polymer (18) | 71 | 24 | 77 | 55 |
| Polymer (19) | 75 | 23 | 81 | 59 |
| Polymer (20) | 73 | 17 | 79 | 62 |

As evident from the above results, the polymer of the compound (1) of the present invention is useful as a water repellent material to form a coating film excellent in water and oil repellency.

INDUSTRIAL APPLICABILITY

The polymer of the present invention is useful as a resist material for lithography (particularly a photosensitive resist material for immersion lithography, a resist protective film material for immersion lithography), a material for an ion exchange membrane, a material for fuel cells, an optical fiber material, electronic components, a transparent resin film material, an adhesive material, a fiber material, a material for a weather resistant coating material, etc.

The entire disclosures of Japanese Patent Application No. 2007-093221 filed on Mar. 30, 2007 and Japanese Patent Application No. 2007-261185 filed on Oct. 4, 2007 including specifications, claims, drawings and summaries are incorporated herein by reference in their entireties.

What is claimed is:

1. A compound represented by the following formula (1):

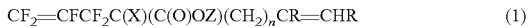

wherein X is a hydrogen atom, a cyano group or a group represented by the formula —C(O)OZ; Z is a hydrogen atom or a $C_{1-20}$ monovalent organic group; n is 0, 1 or 2; and R is a hydrogen atom or a $C_{1-20}$ monovalent organic group, provided that two R's may be the same or different.

2. A compound represented by the following formula (11):

$$CF_2=CFCF_2CH(C(O)OZ^1)CH_2CH=CH_2 \quad (11)$$

wherein $Z^1$ is a hydrogen atom, a group represented by the formula —$C(Y^1)_3$, a group represented by the formula —$CH_2OY^2$ or a group represented by the following formula:

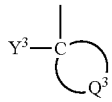

each of $Y^1$ and $Y^2$ which are independent of each other, is a hydrogen atom or a $C_{1-19}$ monovalent saturated hydrocarbon group; $Y^3$ is a hydrogen atom or a $C_{1-16}$ monovalent saturated hydrocarbon group; and $Q^3$ is a $C_{3-19}$ group which forms a bivalent cyclic hydrocarbon group in combination with the carbon atom in the formula, provided that in $Y^1$, $Y^2$ and $Y^3$ in the case of a monovalent saturated hydrocarbon group and $Q^3$, between the carbon atom-carbon atom, a group represented by the formula —O—, a group represented by the formula —C(O)— or a group represented by the formula —C(O)O— may be inserted, and to a carbon atom in $Y^1$, $Y^2$, $Y^3$ and $Q^3$, a fluorine atom, a hydroxyl group or a carboxyl group may be bonded.

3. A compound represented by the following formula (111):

$$CF_2=CFCF_2CH(C(O)OZ^{11})CH_2CH=CH_2 \quad (111)$$

wherein $Z^{11}$ is a hydrogen atom, a group represented by the formula —$C(Y^{11})_3$, a group represented by the formula —$CH_2OY^{21}$ or a group represented by the formula:

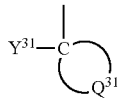

$Y^{11}$ is a $C_{1-6}$ monovalent saturated hydrocarbon group; $Y^{21}$ is a $C_{1-12}$ monovalent saturated hydrocarbon group or a $C_{2-12}$ monovalent saturated hydrocarbon group containing a group represented by the formula —O—; $Y^{31}$ is a hydrogen atom or a $C_{1-6}$ monovalent saturated hydrocarbon group; and $Q^{31}$ is a $C_{4-12}$ a bivalent saturated hydrocarbon group, a $C_{4-12}$ bivalent fluorinated saturated hydrocarbon group or a $C_{4-12}$ bivalent saturated hydrocarbon group having a group represented by the formula —O—, a group represented by the formula —C(O)— or a group represented by the formula —C(O)O— inserted between the carbon atom-carbon atom.

4. A compound represented by the following formula (1111):

$$CF_2=CFCF_2CH(C(O)OZ^{111})CH_2CH=CH_2 \quad (1111)$$

wherein $Z^{111}$ is a $C_{3-20}$ monovalent organic group having at least one group represented by the formula —$C(CF_3)_2OH$.

5. A compound represented by the following formula (12):

$$CF_2=CFCF_2C(C(O)OZ^1)_2CH_2CH=CH_2 \quad (12)$$

wherein $Z^1$ is a hydrogen atom, a group represented by the formula —$C(Y^1)_3$, a group represented by the formula —$CH_2OY^2$ or a group represented by the following formula:

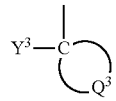

each of $Y^1$ and $Y^2$ which are independent of each other, is a hydrogen atom or a $C_{1-19}$ monovalent saturated hydrocarbon group; $Y^3$ is a hydrogen atom or a $C_{1-6}$ monovalent saturated hydrocarbon group; and $Q^3$ is a $C_{3-19}$ group which forms a bivalent cyclic hydrocarbon group in combination with the carbon atom in the formula, provided that in $Y^1$, $Y^2$ and $Y^3$ in the case of a monovalent saturated hydrocarbon group and $Q^3$, between the carbon atom-carbon atom, a group represented by the formula —O—, a group represented by the formula —C(O)— or a group represented by the formula —C(O)O— may be inserted, and to a carbon atom in $Y^1$, $Y^2$, $Y^3$ and $Q^3$, a fluorine atom, a hydroxyl group or a carboxyl group may be bonded.

6. A compound represented by the following formula (121):

$$CF_2=CFCF_2C(C(O)OZ^{11})_2CH_2CH=CH_2 \quad (121)$$

wherein $Z^{11}$ is a hydrogen atom, a group represented by the formula —$C(Y^{11})_3$, a group represented by the formula —$CH_2OY^{21}$ or a group represented by the following formula:

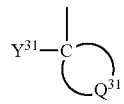

$Y^{11}$ is a $C_{1-6}$ monovalent saturated hydrocarbon group; $Y^{21}$ is a $C_{1-12}$ monovalent saturated hydrocarbon group or a $C_{2-12}$ monovalent saturated hydrocarbon group containing a group represented by the formula —O—; $Y^{31}$ is a hydrogen atom or a $C_{1-6}$ monovalent saturated hydrocarbon group; and $Q^{31}$ is a $C_{4-12}$ a bivalent saturated hydrocarbon group, a $C_{4-12}$ bivalent fluorinated saturated hydrocarbon group or a $C_{4-12}$ bivalent saturated hydrocarbon group having a group represented by the formula —O—, a group represented by the formula —C(O)— or a group represented by the formula —C(O)O— inserted between the carbon atom-carbon atom.

7. A method for producing a compound represented by the following formula (p12), which comprises reacting a compound represented by the following formula (p5) with a compound represented by the following formula (p4) to obtain a compound represented by the following formula (p3), and then reacting the compound with a compound represented by the following formula (p2):

$$CH_2(C(O)OZ^P)_2 \quad (p5)$$

$$CHR=CR(CH_2)_n\text{-}G^P \quad (p4)$$

$$CH(C(O)OZ^P)_2((CH_2)_nCR=CHR) \quad (p3)$$

$$CF_2=CFCF_2\text{-}J^P \quad (p2)$$

$$CF_2=CFCF_2C(C(O)OZ^P)_2(CH_2)_nCR=CHR \quad (p12)$$

wherein $Z^P$ is a $C_{1-20}$ monovalent organic group; R is a hydrogen atom or a $C_{1-20}$ monovalent organic group, provided that two R's may be the same or different; n is 0, 1 or 2; GP is a chlorine atom, a bromine atom or an iodine atom; $J^P$ is a chlorine atom, a bromine atom, an iodine atom or a group represented by the formula $-OSO_2\text{-}L^P$; and $L^P$ is a fluorine atom, a $C_{1-10}$ hydrocarbon group or a $C_{1-10}$ fluorinated hydrocarbon group.

8. A method for producing a compound represented by the following formula (12H), which comprises hydrolyzing a compound represented by the following formula (p12):

$$CF_2=CFCF_2C(C(O)OZ^P)_2(CH_2)_nCR=CHR \quad (p12)$$

$$CF_2=CFCF_2C(C(O)OH)_2(CH_2)_nCR=CHR \quad (12H)$$

wherein $Z^P$ is a $C_{1-20}$ monovalent organic group; R is a hydrogen atom or a $C_{1-20}$ monovalent organic group, provided that two R's may be the same or different; and n is 0, 1 or 2.

9. A method for producing a compound represented by the following formula (11H), which comprises decarboxylation of a compound represented by the following formula (12H):

$$CF_2=CFCF_2C(C(O)OH)_2(CH_2)_nCR=CHR \quad (12H)$$

$$CF_2=CFCF_2CH(C(O)OH)(CH_2)_nCR=CHR \quad (11H)$$

wherein R is a hydrogen atom or a $C_{1-20}$ monovalent organic group, provided that two R's may be the same or different; and n is 0, 1 or 2.

10. A method for producing a compound represented by the following formula (12W), which comprises reacting a compound represented by the following formula (12H) with a compound represented by the following formula (w):

$$CF_2=CFCF_2C(C(O)OH)_2(CH_2)_nCR=CHR \quad (12H)$$

$$CH_2=CW^P_2 \quad (w)$$

$$CF_2=CFCF_2C(C(O)OC(CH_3)W^P_2)_2(CH_2)_nCR=CHR \quad (12W)$$

wherein R is a hydrogen atom or a $C_{1-20}$ monovalent organic group, provided that two R's may be the same or different; n is 0, 1 or 2; and $W^P$ is each independently a hydrogen atom or a $C_{1-20}$ monovalent saturated hydrocarbon group, or two $W^P$'s are groups which form a $C_{3-20}$ bivalent cyclic hydrocarbon group in combination with the carbon atom in the formula.

11. A method for producing a compound represented by the following formula (11W), which comprises reacting a compound represented by the following formula (11H) with a compound represented by the following formula (w):

$$CF_2=CFCF_2CH(C(O)OH)(CH_2)_nCR=CHR \quad (11H)$$

$$CH_2=CW^P_2 \quad (w)$$

$$CF_2=CFCF_2CH(C(O)OC(CH_3)W^P_2)(CH_2)_nCR=CHR \quad (11W)$$

wherein R is a hydrogen atom or a $C_{1-20}$ monovalent organic group, provided that two R's may be the same or different; n is 0, 1 or 2; and $W^P$ is each independently a hydrogen atom or a $C_{1-20}$ monovalent saturated hydrocarbon group, or two $W^P$'s are groups which form a $C_{3-20}$ bivalent cyclic hydrocarbon group in combination with the carbon atom in the formula.

* * * * *